(12) United States Patent
Teramoto et al.

(10) Patent No.: US 7,649,008 B2
(45) Date of Patent: Jan. 19, 2010

(54) CRYSTAL OF BENZIMIDAZOLE DERIVATIVE AND PROCESS FOR PRODUCING THE SAME

(75) Inventors: Mitsuru Teramoto, Iwakuni (JP); Naoki Tsuchiya, Hino (JP); Hiroshi Saitoh, Hino (JP)

(73) Assignee: Teijin Pharma Limited, Tokyo (JP)

( * ) Notice: Subject to any disclaimer, the term of this patent is extended or adjusted under 35 U.S.C. 154(b) by 300 days.

(21) Appl. No.: 10/556,683

(22) PCT Filed: May 14, 2004

(86) PCT No.: PCT/JP2004/006887

§ 371 (c)(1),
(2), (4) Date: Nov. 14, 2005

(87) PCT Pub. No.: WO2004/101551

PCT Pub. Date: Nov. 25, 2004

(65) Prior Publication Data

US 2006/0293375 A1     Dec. 28, 2006

(30) Foreign Application Priority Data

May 14, 2003 (JP) .............................. 2003-135567

(51) Int. Cl.
   *A61K 31/4184*    (2006.01)
   *C07D 235/28*    (2006.01)

(52) U.S. Cl. .................... 514/395; 548/305.1

(58) Field of Classification Search ............... 548/305.1; 514/395
See application file for complete search history.

(56) References Cited

U.S. PATENT DOCUMENTS

| | | | |
|---|---|---|---|
| 4,816,455 A | 3/1989 | Schickaneder et al. | |
| 5,945,450 A | 8/1999 | Takenouchi et al. | |
| 6,774,245 B2 | 8/2004 | Saitoh et al. | |
| 6,884,896 B2 | 4/2005 | Saitoh et al. | |
| 7,176,320 B2 * | 2/2007 | Tsuchiya et al. | 548/305.1 |
| 2004/0010004 A1 | 1/2004 | Tsuchiya et al. | |
| 2004/0122042 A1 * | 6/2004 | Urata et al. | 514/303 |

FOREIGN PATENT DOCUMENTS

| | | |
|---|---|---|
| CA | 2 336 909 A1 | 1/2000 |
| CA | 2 396 908 A1 | 7/2001 |
| CA | 2 442 761 A1 | 3/2003 |
| EP | 0 304 941 B1 | 8/1988 |
| EP | 1 097 926 A1 | 5/2001 |
| EP | 1 249 450 A1 | 10/2002 |
| JP | 62-226980 | 10/1987 |
| JP | 64-71816 | 3/1989 |
| RU | 2 213 743 C2 | 11/2002 |
| RU | 2332417 C2 | 8/2008 |
| WO | 99/52525 A1 | 10/1999 |
| WO | WO 00/03997 A1 | 1/2000 |
| WO | WO 01/53291 A1 | 7/2001 |
| WO | WO 03/18061 A1 | 3/2003 |

OTHER PUBLICATIONS

Byrn et al. (Sold-State Chemistry of Drugs, 2nd Edition, 1999, SSCI, Inc. Publishers).*
Morissette et al. (Adv. Drug Del. Rev. 2004, 56, 275-300).*
Doggrell, S. A. (Expert Opin. Ther. Patents 2008, 18(5), 485-499).*
Aoyama, Y. (Expert Opin. Ther. Patents 2001, 11(9), 1423-1428).*
Takai et al. (European Journal of Pharmacology 2004, 501, 1-8).*
Rouhi. A. G., Chem. & Eng. News, 2003.*
European Office Action dated Nov. 9, 2009 in corresponding European Patent Application No. 04 733 128.5. English.
M. R. Caira, "Crystalline Polymorphism of Organic Compounds," Topics in Current Chemistry, Jan. 1, 1998, pp. 163-208, vol. 198, Springer Verlag Berlin Heidelberg, DE. English.

* cited by examiner

*Primary Examiner*—Rebecca L Anderson
*Assistant Examiner*—Jason Nolan
(74) *Attorney, Agent, or Firm*—Sughrue Mion, PLLC

(57) ABSTRACT

Various crystal forms of 4-(1-((4-methylbenzothiophen-3-yl) methyl)benzimidazol-2-ylthio)butanoic acid from a solvent, and a process for production thereof are provided.

27 Claims, 18 Drawing Sheets

CRYSTAL OF BENZIMIDAZOLE DERIVATIVE AND PROCESS FOR PRODUCING THE SAME

This is a U.S. national stage entry of application Ser. No. PCT/JP2004/006887 filed May 14, 2004.

FIELD OF INVENTION

The present invention relates to a crystal of 4-(1-((4-methylbenzothiophen-3-yl)methyl)benzimidazol-2-ylthio)butanoic acid, a process for producing the same, and a pharmaceutical composition containing the same. This compound has a chymase inhibitory activity in the living body and can be used as a preventive and/or remedy for inflammatory diseases, allergic diseases, respiratory tract diseases, circulatory diseases, or bone and/or cartilage metabolic diseases.

BACKGROUND ART

When a certain compound has two or more kinds of crystal forms, these different crystal forms are referred to as crystal polymorphism. It is commonly known that stability varies with each crystal form of crystal polymorphism. For example, Japanese Unexamined Patent Publication (Kokai) No. 62-226980 describes that two kinds of crystal forms of prazosin hydrochloride have different stabilities and exert an influence on the results of long-term storage stability. Also Japanese Unexamined Patent Publication (Kokai) No. 64-71816 describes that a specific crystal form among different crystal forms of buspirone hydrochloride is advantageous in view of retention of specific physical properties during storage or under manufacturing conditions.

In the production of a drug substance for medicine, it is advantageous for the storage stability and control of manufacturing process of the drug substance and pharmaceutical composition to obtain the drug substance in a crystal form.

In case a compound having two or more crystal forms is employed as a medicine, physicochemical properties such as melting point, solubility and stability, and pharmacokinetics such as, absorptivity, distribution, metabolism and excretion vary with each crystal, and thus biological properties such as appearance of drug efficacy vary sometimes. To ensure that the resulting medicine has stable properties described above, it is often required to produce a drug substance having a specific crystal form. Also in the process for production of the drug substance, it is important to precipitate a specific crystal form in the crystallization operation so as to maintain the yield and purification effect.

It is impossible to anticipate the presence of crystal polymorphism by the structure of the compound, and it is considered to be important to find out a crystal form in the development of the medicine.

As described in WO 00/03997 and WO 01/53291, it is known that 4-(1-((4-methylbenzothiophen-3-yl)methyl)benzimidazol-2-ylthio)butanoic acid represented by the following formula (I) has an effect of inhibiting chymase.

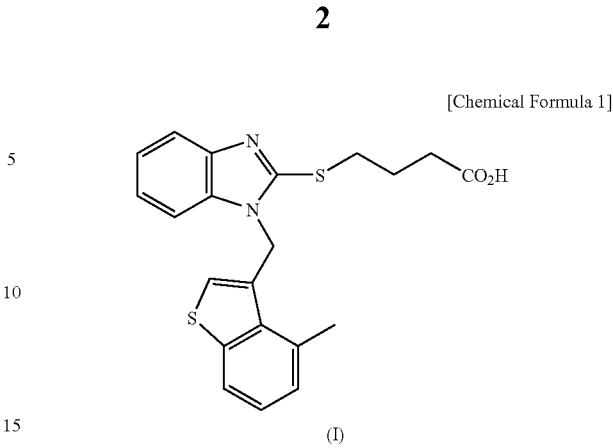

[Chemical Formula 1]

(I)

However, there is not any description about the crystal or crystal polymorphism in the above references.

Chymase is one of neutral proteinases present in mast cell granules and has a close relation with various vital reactions associated with mast cells. There have been reported various effects, for example, acceleration of degranulation from mast cells, activation of Interleukin-1-$\beta$ (IL-1$\beta$), activation of matrix protease, decomposition of fibronectin and IV type collagen, acceleration of release of Transforming growth factor-$\beta$ (TGF-$\beta$), activation of material P and bathoactive intestinal polypeptide (VIP), effect of conversion from Angiotensin (Ang I) into Ang II, and Endothelin conversion effect. As is apparent from the above description, it is considered that an activity inhibitor against chymase is useful as a preventive and/or a remedy for respiratory tract diseases such as bronchial asthma; inflammatory and/or allergic diseases such as allergic rhinitis, atopic dermatitis, and urticaria; circulatory diseases such as sclerosing vascular lesion, intravascular stricture, peripheral circulatory disturbance, renal insufficiency, and cardiac insufficiency; and bone and/or cartilage metabolism diseases such as rheumatism and osteoarthritis.

DISCLOSURE OF THE INVENTION

An object of the present invention is to provide a crystal of 4-(1-((4-methylbenzothiophen-3-yl)methyl)benzimidazol-2-ylthio)butanoic acid or a solvate thereof.

Another object of the present invention is to provide a process for producing a crystal of 4-(1-((4-methylbenzothiophen-3-yl)methyl)benzimidazol-2-ylthio)butanoic acid or a solvate thereof.

Still another object of the present invention is to provide a preventive and/or remedy for inflammatory diseases, allergic diseases, respiratory tract diseases, circulatory diseases and bone and/or cartilage metabolic diseases, having a chymase inhibitory activity.

The present inventors have intensively studied and found that four kinds of crystal forms exist and five kinds of solvates exist as crystals, in 4-(1-((4-methylbenzothiophen-3-yl)methyl)benzimidazol-2-ylthio)butanoic acid and, furthermore, any crystals are suited for use as a drug substance or a production intermediate of the pharmaceutical composition of the present invention, and thus the present invention has been completed.

The present invention provides (1) a crystal of 4-(1-((4-methylbenzothiophen-3-yl)methyl)benzimidazol-2-ylthio) butanoic acid or a solvate thereof.

The present invention also provides (2) a crystal of 4-(1-((4-methylbenzothiophen-3-yl)methyl)benzimidazol-2-ylthio)butanoic acid (crystal A), which yields a powder X-ray diffraction pattern having characteristic peaks at reflection angles 2θ of approximately 9.0°, 15.2°, 16.4°, 19.2°, 20.6°, 22.3° and 22.6°, that is, (3) a crystal of 4-(1-((4-methylbenzothiophen-3-yl)methyl)benzimidazol-2-ylthio)butanoic acid (crystal A), which yields a powder X-ray diffraction pattern shown virtually in FIG. 1.

The present invention also provides (4) a crystal of 4-(1-((4-methylbenzothiophen-3-yl)methyl)benzimidazol-2-ylthio)butanoic acid (crystal B), which yields a powder X-ray diffraction pattern having characteristic peaks at reflection angles 2θ of approximately 14.1°, 17.7°, 18.6°, 22.3°, 23.5°, 24.3° and 26.2°, that is, (5) a crystal of 4-(1-((4-methylbenzothiophen-3-yl)methyl)benzimidazol-2-ylthio)butanoic acid (crystal B), which yields a powder X-ray diffraction pattern shown virtually in FIG. 2.

The present invention also provides (6) a crystal of 4-(1-((4-methylbenzothiophen-3-yl)methyl)benzimidazol-2-ylthio)butanoic acid (crystal D), which yields a powder X-ray diffraction pattern having characteristic peaks at reflection angles 2θ of approximately 11.4°, 13.8°, 16.7°, 22.4°, 23.9° and 25.5°, that is, (7) a crystal of 4-(1-((4-methylbenzothiophen-3-yl)methyl)benzimidazol-2-ylthio)butanoic acid (crystal D), which yields a powder X-ray diffraction pattern shown virtually in FIG. 3.

The present invention also provides (8) a crystal of 4-(1-((4-methylbenzothiophen-3-yl)methyl)benzimidazol-2-ylthio)butanoic acid (crystal E), which yields a powder X-ray diffraction pattern having characteristic peaks at reflection angles 2θ of approximately 16.4°, 16.8°, 19.6°, 20.4°, 21.5°, 22.6°, 23.4° and 24.1°, that is, (9) a crystal of 4-(1-((4-methylbenzothiophen-3-yl)methyl)benzimidazol-2-ylthio)butanoic acid (crystal E), which yields a powder X-ray diffraction pattern shown virtually in FIG. 4.

The present invention also provides (10) a crystal of 4-(1-((4-methylbenzothiophen-3-yl)methyl)benzimidazol-2-ylthio)butanoic acid hydrate (hydrate crystal), which yields a powder X-ray diffraction pattern having characteristic peaks at reflection angles 2θ of approximately 10.3°, 15.2°, 15.8°, 21.0°, 23.1°, 24.2° and 25.1°, that is, (11) a crystal of 4-(1-((4-methylbenzothiophen-3-yl)methyl)benzimidazol-2-ylthio)butanoic acid hydrate (hydrate crystal), which yields a powder X-ray diffraction pattern shown virtually in FIG. 5.

The present invention also provides (12) a crystal of 4-(1-((4-methylbenzothiophen-3-yl)methyl)benzimidazol-2-ylthio)butanoic acid methanolate (methanolate crystal), which yields a powder X-ray diffraction pattern having characteristic peaks at reflection angles 2θ of approximately 7.8°, 12.4°, 17.3°, 25.0° and 25.8°, that is, (13) a crystal of 4-(1-((4-methylbenzothiophen-3-yl)methyl)benzimidazol-2-ylthio)butanoic acid methanolate (methanolate crystal), which yields a powder X-ray diffraction pattern shown virtually in FIG. 6.

The present invention also provides (14) a crystal of 4-(1-((4-methylbenzothiophen-3-yl)methyl)benzimidazol-2-ylthio)butanoic acid ethanolate (ethanolate crystal), which yields a powder X-ray diffraction pattern having characteristic peaks at reflection angles 2θ of approximately 7.8°, 12.1°, 17.2°, 20.4°, 20.6°, 22.9°, 24.4° and 25.5°, that is, (15) a crystal of 4-(1-((4-methylbenzothiophen-3-yl)methyl)benzimidazol-2-ylthio)butanoic acid ethanolate (ethanolate crystal), which yields a powder X-ray diffraction pattern shown virtually in FIG. 7.

The present invention also provides (16) a crystal of 4-(1-((4-methylbenzothiophen-3-yl)methyl)benzimidazol-2-ylthio)butanoic acid 1-propanolate (1-propanolate crystal), which yields a powder X-ray diffraction pattern having characteristic peaks at reflection angles 2θ of approximately 7.7°, 12.1°, 17.1°, 20.5°, 22.4° and 25.0°, that is, (17) a crystal of 4-(1-((4-methylbenzothiophen-3-yl)methyl)benzimidazol-2-ylthio)butanoic acid 1-propanolate (1-propanolate crystal), which yields a powder X-ray diffraction pattern shown virtually in FIG. 8.

The present invention also provides (18) a crystal of 4-(1-((4-methylbenzothiophen-3-yl)methyl)benzimidazol-2-ylthio)butanoic acid 2-propanolate (2-propanolate crystal), which yields a powder X-ray diffraction pattern having characteristic peaks at reflection angles 2θ of approximately 7.8°, 12.0°, 17.1°, 20.1°, 20.6°, 22.7°, 24.0° and 25.2°, that is, (19) a crystal of 4-(1-((4-methylbenzothiophen-3-yl)methyl)benzimidazol-2-ylthio)butanoic acid 2-propanolate (2-propanolate crystal), which yields a powder X-ray diffraction pattern shown virtually in FIG. 9.

The present invention also provides (20) a crystal of 4-(1-((4-methylbenzothiophen-3-yl)methyl)benzimidazol-2-ylthio)butanoic acid (crystal A), which has peaks at wave numbers of approximately 1711, 1442, 1285, 1252, 1204, 771 and 750 cm$^{-1}$ in an infrared absorption spectrum in potassium bromide, that is, (21) a crystal of 4-(1-((4-methylbenzothiophen-3-yl)methyl)benzimidazol-2-ylthio)butanoic acid (crystal A), which yields an absorption pattern shown in FIG. 10 in an infrared absorption spectrum in potassium bromide.

The present invention also provides (22) a crystal of 4-(1-((4-methylbenzothiophen-3-yl)methyl)benzimidazol-2-ylthio)butanoic acid (crystal B), which has peaks at wave numbers of approximately 1716, 1701, 1290, 1252, 1207, 1151, 768 and 743 cm$^{-1}$ in an infrared absorption spectrum in potassium bromide, that is, (23) a crystal of 4-(1-((4-methylbenzothiophen-3-yl)methyl)benzimidazol-2-ylthio)butanoic acid (crystal B) which yields an absorption pattern shown in FIG. 11 in an infrared absorption spectrum in potassium bromide.

The present invention also provides (24) a crystal of 4-(1-((4-methylbenzothiophen-3-yl)methyl)benzimidazol-2-ylthio)butanoic acid (crystal D), which has peaks at wave numbers of approximately 1703, 1441, 1383, 1321, 1245, 1196, 766 and 746 cm$^{-1}$ in an infrared absorption spectrum in potassium bromide, that is, (25) a crystal of 4-(1-((4-methylbenzothiophen-3-yl)methyl)benzimidazol-2-ylthio)butanoic acid (crystal D), which yields an absorption pattern shown in FIG. 12 in an infrared absorption spectrum in potassium bromide.

The present invention also provides (26) a crystal of 4-(1-((4-methylbenzothiophen-3-yl)methyl)benzimidazol-2-ylthio)butanoic acid (crystal E), which has peaks at wave numbers of approximately 1716, 1286, 1221, 1196, 1144, 761 and 742 cm$^{-1}$ in an infrared absorption spectrum in potassium bromide, that is, (27) a crystal of 4-(1-((4-methylbenzothiophen-3-yl)methyl)benzimidazol-2-ylthio)butanoic acid (crystal E), which yields an absorption pattern shown in FIG. 13 in an infrared absorption spectrum in potassium bromide.

The present invention also provides (28) a crystal of 4-(1-((4-methylbenzothiophen-3-yl)methyl)benzimidazol-2-ylthio)butanoic acid hydrate crystal (hydrate crystal), which has peaks at wave numbers of approximately 1705, 1310, 1288, 1248, 1194, 760 and 746 cm$^{-1}$ in an infrared absorption spectrum in potassium bromide, that is, (29) a crystal of 4-(1-((4-methylbenzothiophen-3-yl)methyl)benzimidazol-2-ylthio)butanoic acid hydrate (hydrate crystal), which yields an absorption pattern shown in FIG. 14 in an infrared absorption spectrum in potassium bromide.

The present invention also provides (30) a crystal of 4-(1-((4-methylbenzothiophen-3-yl)methyl)benzimidazol-2- ylthio)butanoic acid methanolate (methanolate crystal), which has peaks at wave numbers of approximately 1728, 1444, 1250, 1190, 1038, 764 and 748 cm$^{-1}$ in an infrared absorption spectrum in potassium bromide, that is, (31) a crystal of 4-(1-((4-methylbenzothiophen-3-yl)methyl)benzimidazol-2-ylthio)butanoic acid methanolate (methanolate crystal), which yields an absorption pattern shown in FIG. 15 in an infrared absorption spectrum in potassium bromide.

The present invention also provides (32) a crystal of 4-(1-((4-methylbenzothiophen-3-yl)methyl)benzimidazol-2-ylthio)butanoic acid ethanolate (ethanolate crystal), which has peaks at wave numbers of approximately 1724, 1444, 1250, 1194, 1047, 766 and 746 cm$^{-1}$ in an infrared absorption spectrum in potassium bromide, that is, (33) a crystal of 4-(1-((4-methylbenzothiophen-3-yl)methyl)benzimidazol-2-ylthio)butanoic acid ethanolate (ethanolate crystal), which yields an absorption pattern shown in FIG. 16 in an infrared absorption spectrum in potassium bromide.

The present invention also provides (34) a crystal of 4-(1-((4-methylbenzothiophen-3-yl)methyl)benzimidazol-2-ylthio)butanoic acid 1-propanolate (1-propanolate crystal), which has peaks at wave numbers of approximately 1722, 1444, 1252, 1195, 974, 764 and 744 cm$^{-1}$ in an infrared absorption spectrum in potassium bromide, that is, (35) a crystal of 4-(1-((4-methylbenzothiophen-3-yl)methyl)benzimidazol-2-ylthio)butanoic acid 1-propanolate (1-propanolate crystal), which yields an absorption pattern shown in FIG. 17 in an infrared absorption spectrum in potassium bromide.

The present invention also provides (36) a crystal of 4-(1-((4-methylbenzothiophen-3-yl)methyl)benzimidazol-2-ylthio)butanoic acid 2-propanolate (2-propanolate crystal), which has peaks at wave numbers of approximately 1722, 1444, 1250, 1198, 953, 766 and 744 cm$^{-1}$ in an infrared absorption spectrum in potassium bromide, that is, (37) a crystal of 4-(1-((4-methylbenzothiophen-3-yl)methyl)benzimidazol-2-ylthio)butanoic acid 2-propanolate (2-propanolate crystal), which yields an absorption pattern shown in FIG. 18 in an infrared absorption spectrum in potassium bromide.

Specific examples of the crystal form of the present invention include:

(38) a solvate of 4-(1-((4-methylbenzothiophen-3-yl)methyl)benzimidazol-2-ylthio)butanoic acid;

(39) a hydrate of 4-(1-((4-methylbenzothiophen-3-yl)methyl)benzimidazol-2-ylthio)butanoic acid;

(40) a methanolate of 4-(1-((4-methylbenzothiophen-3-yl)methyl)benzimidazol-2-ylthio)butanoic acid;

(41) an ethanolate of 4-(1-((4-methylbenzothiophen-3-yl)methyl)benzimidazol-2-ylthio)butanoic acid;

(42) 1-propanolate of 4-(1-((4-methylbenzothiophen-3-yl)methyl)benzimidazol-2-ylthio)butanoic acid; and

(43) a 2-propanolate of 4-(1-((4-methylbenzothiophen-3-yl)methyl)benzimidazol-2-ylthio)butanoic acid.

The present invention also provides:

(44) a process for producing a crystal B, which comprises performing cooling crystallization from a solution of 4-(1-((4-methylbenzothiophen-3-yl)methyl)benzimidazol-2-ylthio)butanoic acid, and acetic acid, tetrahydrofuran, methanol, 2-butanone, water, or a mixed solvent of two or more kinds selected from them;

(45) a process for producing a crystal B, which comprises adding a small amount of the crystal B as a seed crystal in cooling crystallization from a solution of 4-(1-((4-methylbenzothiophen-3-yl)methyl)benzimidazol-2-ylthio)butanoic acid, and acetic acid, tetrahydrofuran, methanol, 2-butanone, water, or a mixed solvent of two or more kinds selected from them;

(46) a process for producing a crystal D, which comprises adding a small amount of the crystal D as a seed crystal in cooling crystallization from a solution of 4-(1-((4-methylbenzothiophen-3-yl)methyl)benzimidazol-2-ylthio)butanoic acid, and acetic acid, tetrahydrofuran, methanol, 2-butanone, water, or a mixed solvent of two or more kinds selected from them;

(47) a process for producing a crystal D, which comprises performing crystallization by adding water as a poor solvent, to an acetic acid solution of 4-(1-((4-methylbenzothiophen-3-yl)methyl)benzimidazol-2-ylthio)butanoic acid;

(48) a process for producing a crystal D, which comprises performing crystallization by adding a nonpolar hydrocarbon as a poor solvent, to an acetic acid solution of 4-(1-((4-methylbenzothiophen-3-yl)methyl)benzimidazol-2-ylthio)butanoic acid;

(49) the process for producing a crystal D according to (48), wherein the nonpolar hydrocarbon is pentane, hexane, cyclohexane, heptane, or a mixed solvent of two or more kinds selected from them;

(50) a process for producing a crystal B, which comprises performing neutralization crystallization by adding acid to a solution of an alkali metal salt of 4-(1-((4-methylbenzothiophen-3-yl)methyl)benzimidazol-2-ylthio)butanoic acid and water, and tetrahydrofuran, methanol, 2-butanone, or a mixed solvent of two or more kinds selected from them while maintaining at about 50° C. or higher;

(51) a process for producing a hydrate crystal, which comprises performing neutralization crystallization by adding acid to a solution of an alkali metal salt of 4-(1-((4-methylbenzothiophen-3-yl)methyl)benzimidazol-2-ylthio)butanoic acid and water, and tetrahydrofuran, methanol, 2-butanone, or a mixed solvent of two or more kinds selected from them while maintaining at about 40° C. or lower;

(52) a process for producing a crystal E, which comprises drying a hydrate crystal of 4-(1-((4-methylbenzothiophen-3-yl)methyl)benzimidazol-2-ylthio)butanoic acid;

(53) a process for producing a methanolate crystal, which comprises performing cooling crystallization from a solution of 4-(1-((4-methylbenzothiophen-3-yl)methyl)benzimidazol-2-ylthio)butanoic acid, and a solvent containing methanol as a main ingredient;

(54) a process for producing a methanolate crystal, which comprises contacting methanol with a crystal E or a hydrate crystal of 4-(1-((4-methylbenzothiophen-3-yl)methyl)benzimidazol-2-ylthio)butanoic acid, or a mixture thereof;

(55) a process for producing an ethanolate crystal, which comprises performing cooling crystallization from a solution of 4-(1-((4-methylbenzothiophen-3-yl)methyl)benzimidazol-2-ylthio)butanoic acid, and a solvent containing ethanol as a main ingredient;

(56) a process for producing an ethanolate crystal, which comprises contacting ethanol with a crystal E or a hydrate crystal of 4-(1-((4-methylbenzothiophen-3-yl)methyl)benzimidazol-2-ylthio)butanoic acid, or a mixture thereof;

(57) a process for producing a 1-propanolate crystal, which comprises performing cooling crystallization from a solution of 4-(1-((4-methylbenzothiophen-3-yl)methyl)benzimidazol-2-ylthio)butanoic acid, and a solvent containing 1-propanol as a main ingredient;

(58) a process for producing a 1-propanolate crystal, which comprises contacting 1-propanol with a crystal E or a hydrate crystal of 4-(1-((4-methylbenzothiophen-3-yl)methyl)benzimidazol-2-ylthio)butanoic acid, or a mixture thereof;

(59) a process for producing a 2-propanolate crystal, which comprises performing cooling crystallization from a solution of 4-(1-((4-methylbenzothiophen-3-yl)methyl)benzimidazol-2-ylthio)butanoic acid, and a solvent containing 2-propanol as a main ingredient;

(60) a process for producing a 2-propanolate crystal, which comprises contacting 2-propanol with a crystal E or a hydrate crystal of 4-(1-((4-methylbenzothiophen-3-yl)methyl)benzimidazol-2-ylthio)butanoic acid, or a mixture thereof; and

(61) a process for producing a crystal D, which comprises suspending a crystal of 4-(1-((4-methylbenzothiophen-3-yl)methyl)benzimidazol-2-ylthio)butanoic acid or a solvate thereof, or a mixed crystal of two or more kinds selected from them in acetic acid, methyl acetate, ethyl acetate, propyl acetate, isopropyl acetate, butyl acetate, 4-methyl-2-pentanone, 2-butanone, acetone, tetrahydrofuran, acetonitrile, hexane, cyclohexane, heptane, toluene, xylene, methanol, ethanol, 1-propanol, 2-propanol, water, or a mixed solvent of two or more kinds selected from them.

The present invention also provides (62) a pharmaceutical composition comprising the crystal of any one of (1) to (37), or a mixture of two or more kinds selected from them as an active pharmaceutical ingredients.

The present invention further provides (63) a chymase inhibitor comprising the crystal of any one of (1) to (37), or a mixture of two or more kinds selected from them as an active ingredient.

The present invention further provides (64) a preventive and/or a remedy for inflammatory diseases, allergic diseases, respiratory tract diseases, circulatory diseases, or bone and/or cartilage metabolic diseases, comprising the crystal of any one of (1) to (37), or a mixture of two or more kinds selected from them as an active ingredient.

PREFERRED MODE OF THE INVENTION

The crystal of the present invention is characterized by a powder X-ray diffraction pattern and/or an infrared absorption peak in potassium bromide and the like. These crystals yield a characteristic powder X-ray diffraction pattern (XRD) and each crystal has a specific value of 2θ. These crystals also yield a specific absorption pattern in infrared spectrophotometry (IR).

Figure 1:
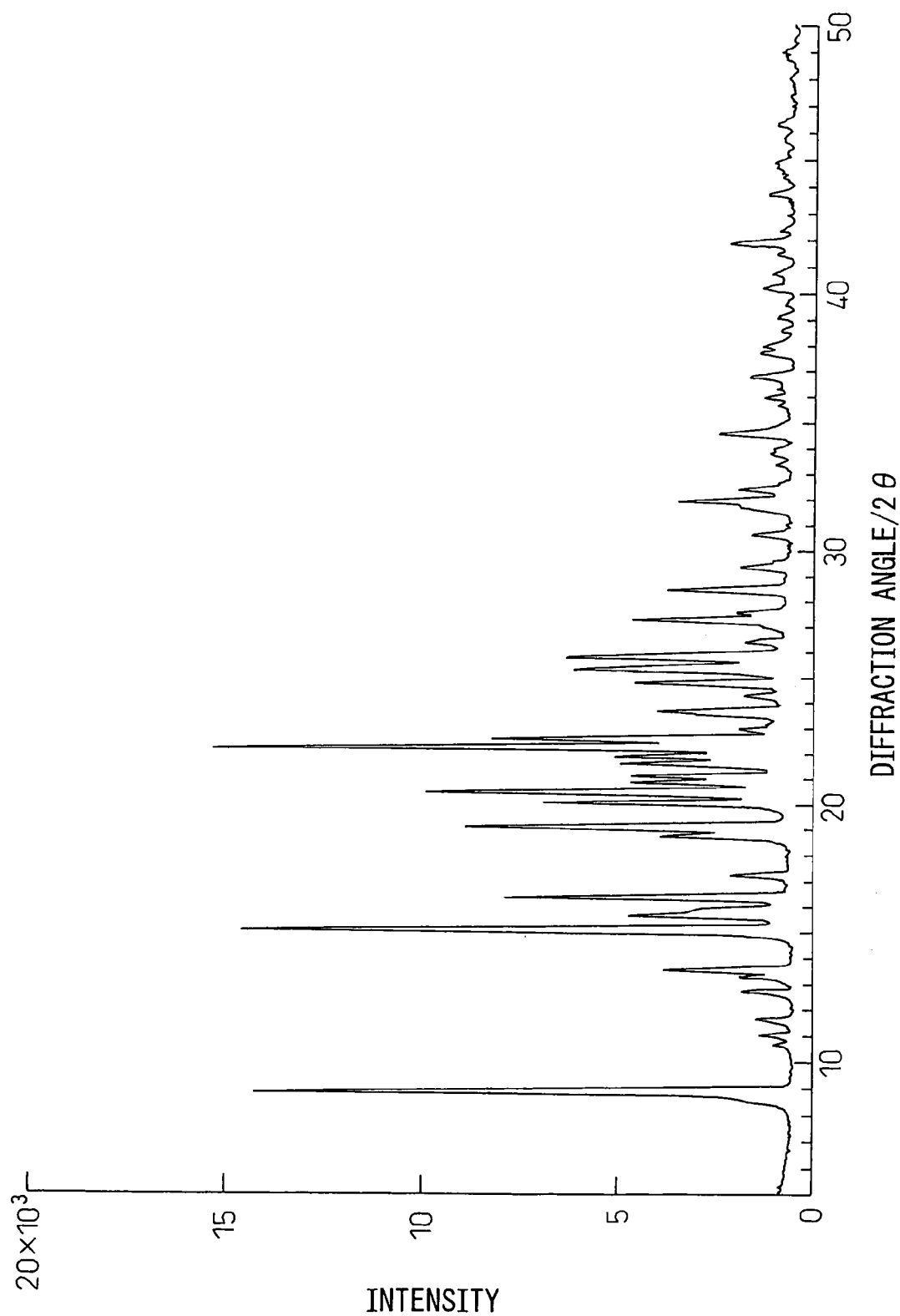
FIG. 1 is a graph showing XRD of a crystal A of the present invention.

The crystal A of the present invention yields a powder X-ray diffraction pattern at reflection angles 2θ of approximately 9.0°, 15.2°, 16.4°, 19.2°, 20.6°, 22.3° and 22.6° and, more specifically, it yields a powder X-ray diffraction pattern having a characteristic peak shown in Table 1 (see FIG. 1). In a powder X-ray diffraction pattern intensity in the table, $I_{max}$ denotes an intensity of a peak having a largest intensity of each crystal and I denotes an intensity of each peak. The value of 2θ of the powder X-ray diffraction pattern can vary by approximately 0.5° with the state of samples and measuring conditions. Because of properties of data of the powder X-ray diffraction pattern, general pattern is important in the identification of crystal form. Since a relative intensity can slightly vary with the growth direction of crystals, size of particles and measuring conditions, it should not be strictly understood.

TABLE 1

A

| Diffraction angle (2θ, °) | Intensity ($I/I_{max}*100$) |
| --- | --- |
| 9.0 | 100 |
| 15.2 | 91 |
| 16.4 | 54 |
| 19.2 | 59 |
| 20.6 | 63 |
| 22.3 | 77 |
| 22.6 | 59 |

Figure 2:
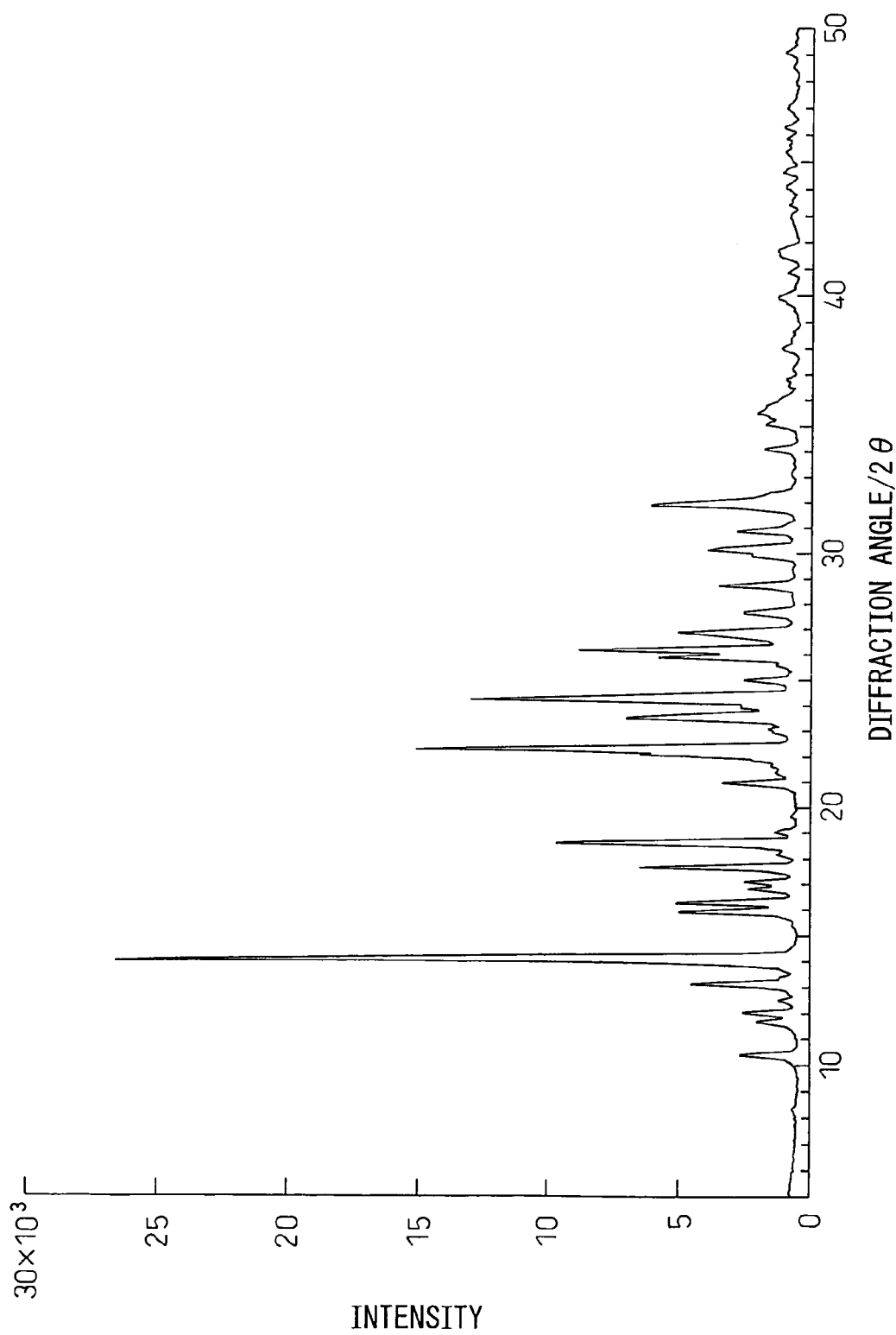
FIG. 2 is a graph showing XRD of a crystal B of the present invention.

The crystal B of the present invention yields a powder X-ray diffraction pattern at reflection angles 2θ of approximately 14.1°, 17.7°, 18.6°, 22.3°, 23.5°, 24.3° and 26.2° and, more specifically, it yields a powder X-ray diffraction pattern having a characteristic peak shown in Table 2 (see FIG. 2).

TABLE 2

B

| Diffraction angle (2θ, °) | Intensity ($I/I_{max}*100$) |
| --- | --- |
| 14.1 | 100 |
| 17.7 | 23 |
| 18.6 | 31 |
| 22.3 | 55 |
| 23.5 | 29 |
| 24.3 | 49 |
| 26.2 | 34 |

Figure 3:
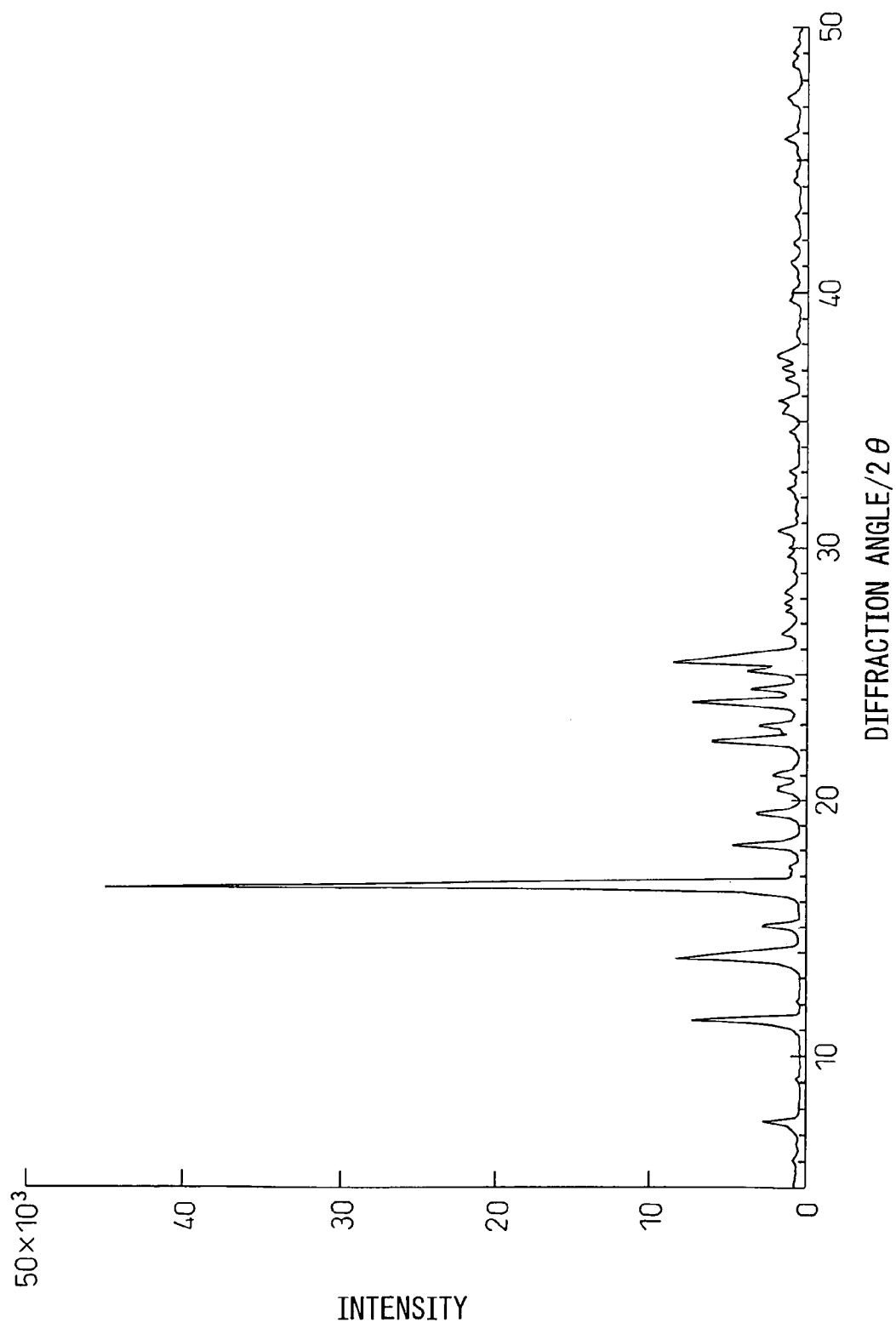
FIG. 3 is a graph showing XRD of a crystal D of the present invention.

The crystal D of the present invention yields a powder X-ray diffraction pattern at reflection angles 2θ of approximately 11.4°, 13.8°, 16.7°, 22.4°, 23.9° and 25.5° and, more specifically, it yields a powder X-ray diffraction pattern having a characteristic peak shown in Table 3 (see FIG. 3).

TABLE 3

| D | |
|---|---|
| Diffraction angle (2θ, °) | Intensity (I/I$_{max}$*100) |
| 11.4 | 16 |
| 13.8 | 25 |
| 16.7 | 100 |
| 22.4 | 18 |
| 23.9 | 23 |
| 25.5 | 22 |

Figure 4:
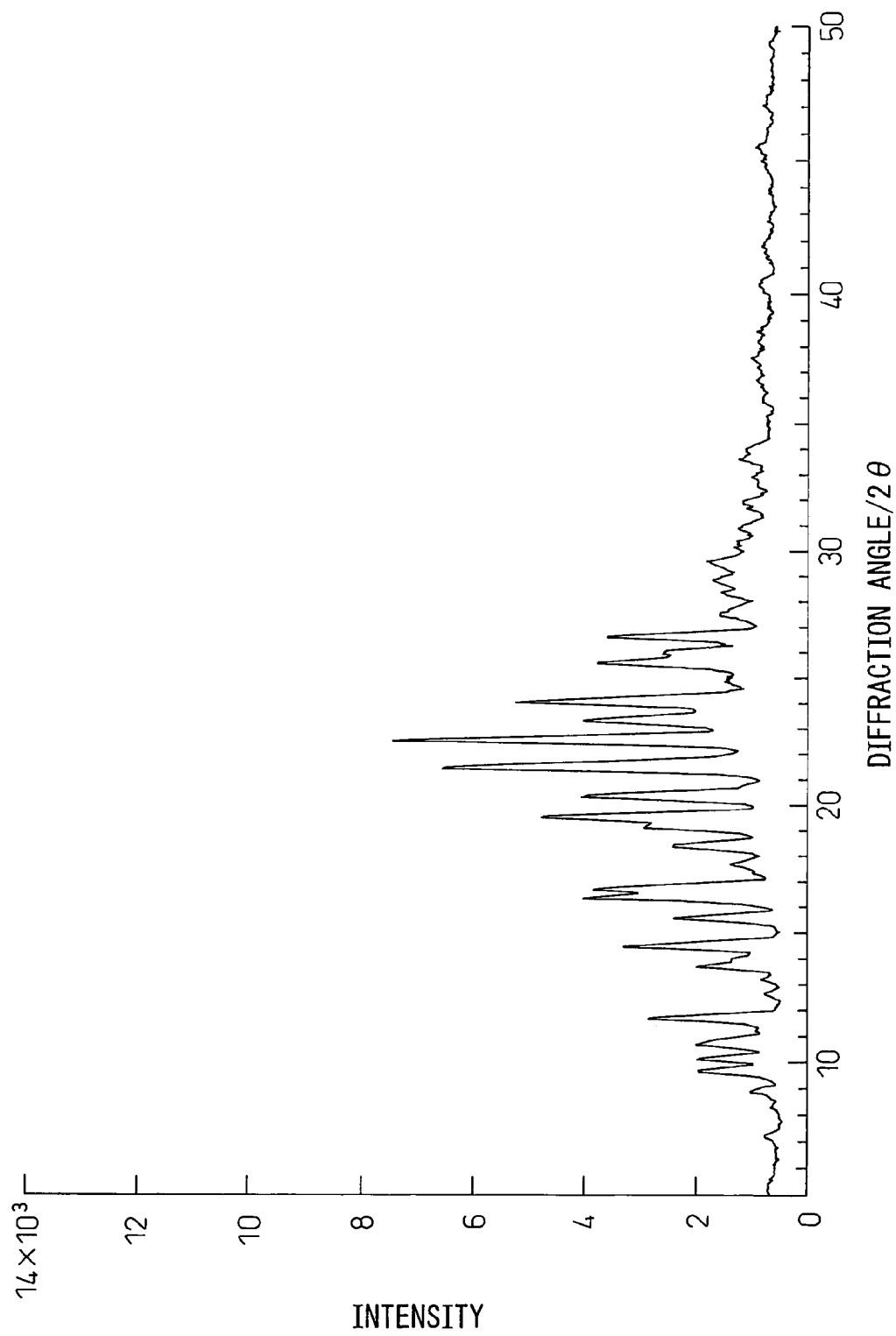
FIG. 4 is a graph showing XRD of a crystal E of the present invention.

The crystal E of the present invention yields a powder X-ray diffraction pattern at reflection angles 2θ of approximately 16.4°, 16.8°, 19.6°, 20.4°, 21.5°, 22.6°, 23.4° and 24.1° and more specifically, it yields a powder X-ray diffraction pattern having a characteristic peak shown in Table 4 (see FIG. 4).

TABLE 4

| E | |
|---|---|
| Diffraction angle (2θ, °) | Intensity (I/I$_{max}$*100) |
| 16.4 | 58 |
| 16.8 | 53 |
| 19.6 | 67 |
| 20.4 | 54 |
| 21.5 | 89 |
| 22.6 | 100 |
| 23.4 | 52 |
| 24.1 | 68 |

Figure 5:
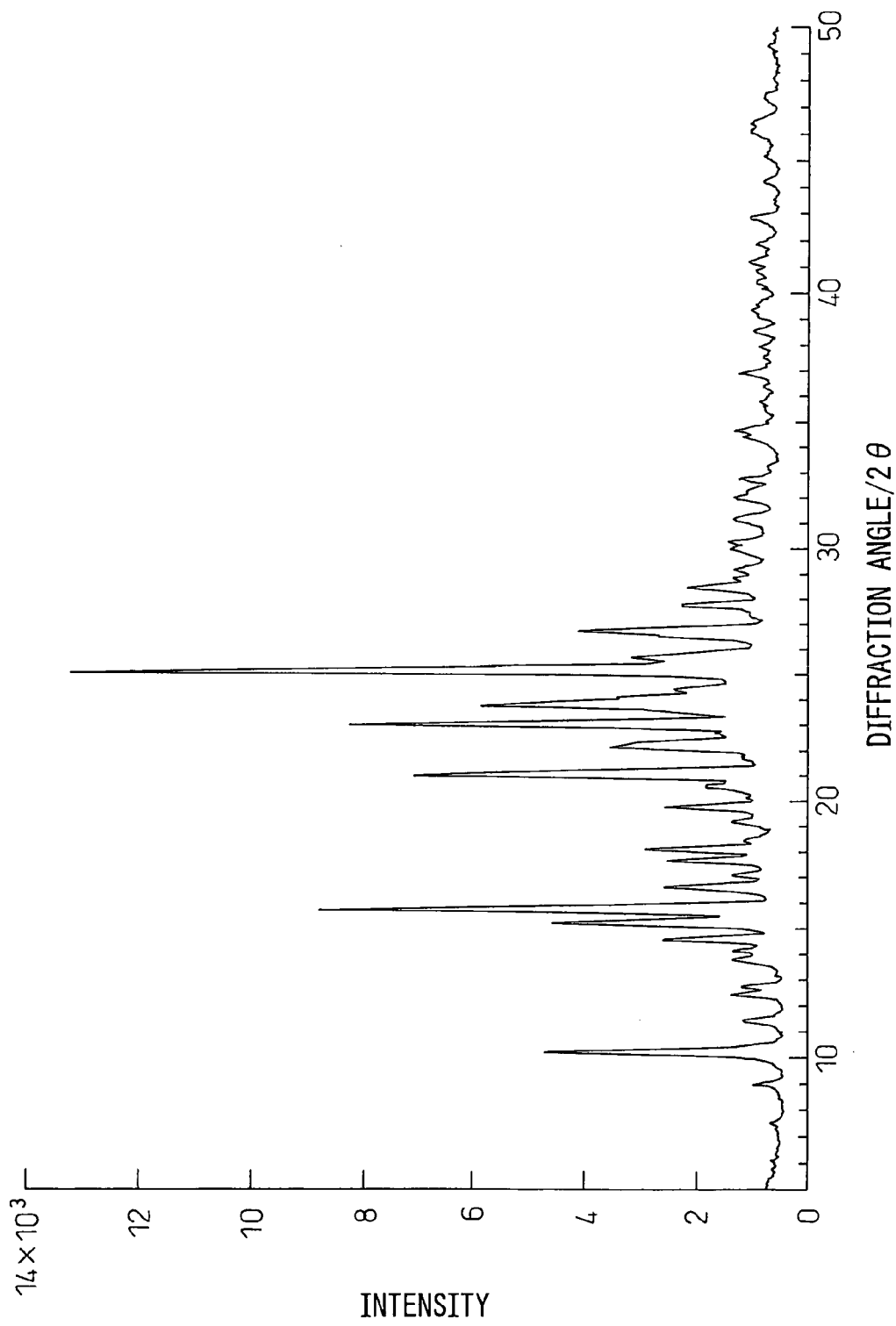
FIG. 5 is a graph showing XRD of a hydrate crystal of the present invention.

The hydrate crystal of the present invention yields a powder X-ray diffraction pattern at reflection angles 2θ of approximately 10.3°, 15.2°, 15.8°, 21.0°, 23.1°, 24.2° and 25.1° and, more specifically, it yields a powder X-ray diffraction pattern having a characteristic peak shown in Table 5 (see FIG. 5).

TABLE 5

| hydrate | |
|---|---|
| Diffraction angle (2θ, °) | Intensity (I/I$_{max}$*100) |
| 10.3 | 43 |
| 15.2 | 36 |
| 15.8 | 70 |
| 21.0 | 58 |
| 23.1 | 70 |
| 24.2 | 34 |
| 25.1 | 100 |

Figure 6:
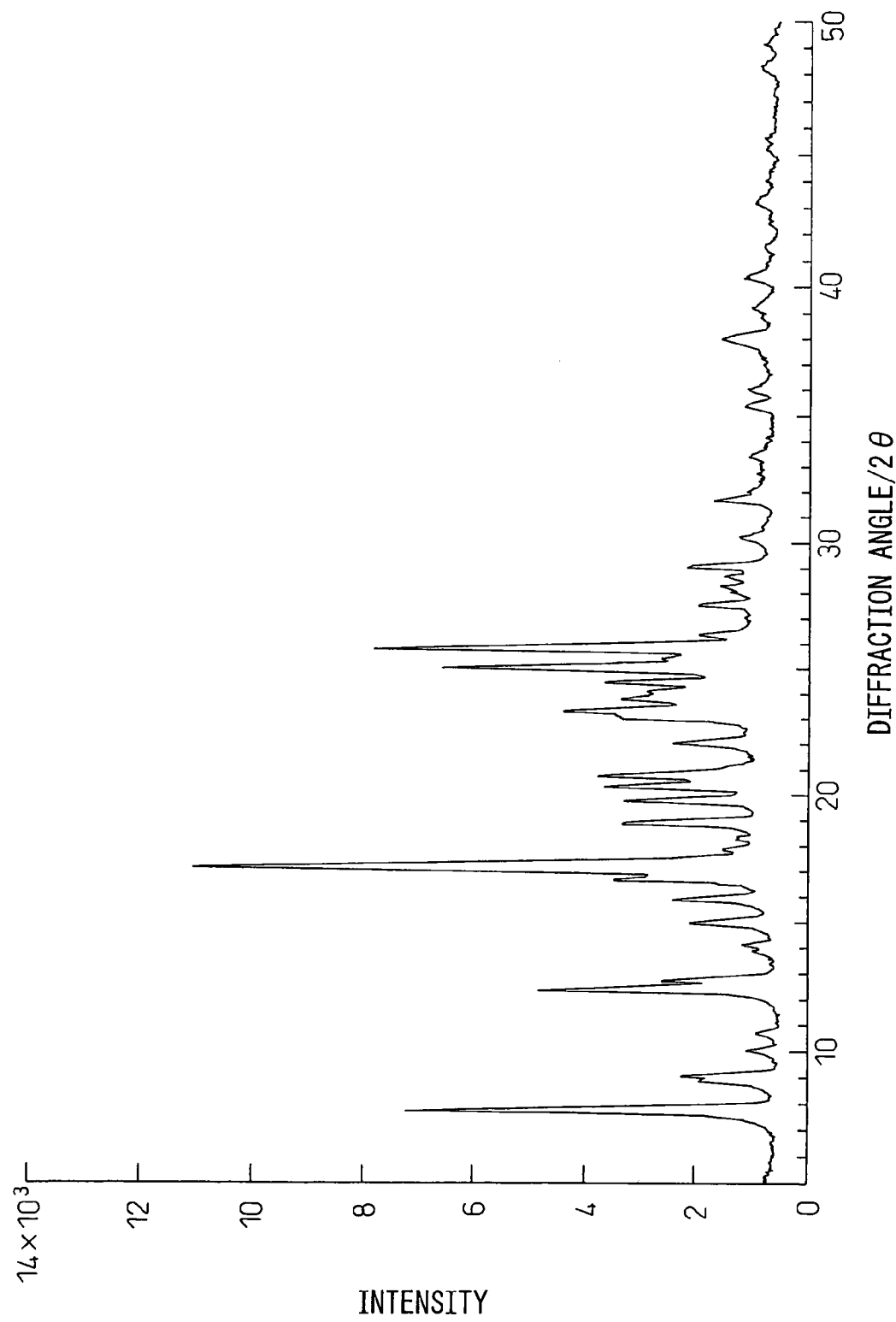
FIG. 6 is a graph showing XRD of a methanolate crystal of the present invention.

The methanolate crystal of the present invention yields a powder X-ray diffraction pattern at reflection angles 2θ of approximately 7.8°, 12.4°, 17.3°, 25.0° and 25.8° and, more specifically, it yields a powder X-ray diffraction pattern having a characteristic peak shown in Table 6 (see FIG. 6).

TABLE 6

| Methanolate | |
|---|---|
| Diffraction angle (2θ, °) | Intensity (I/I$_{max}$*100) |
| 7.8 | 61 |
| 12.4 | 40 |
| 17.3 | 100 |
| 25.0 | 55 |
| 25.8 | 61 |

Figure 7:
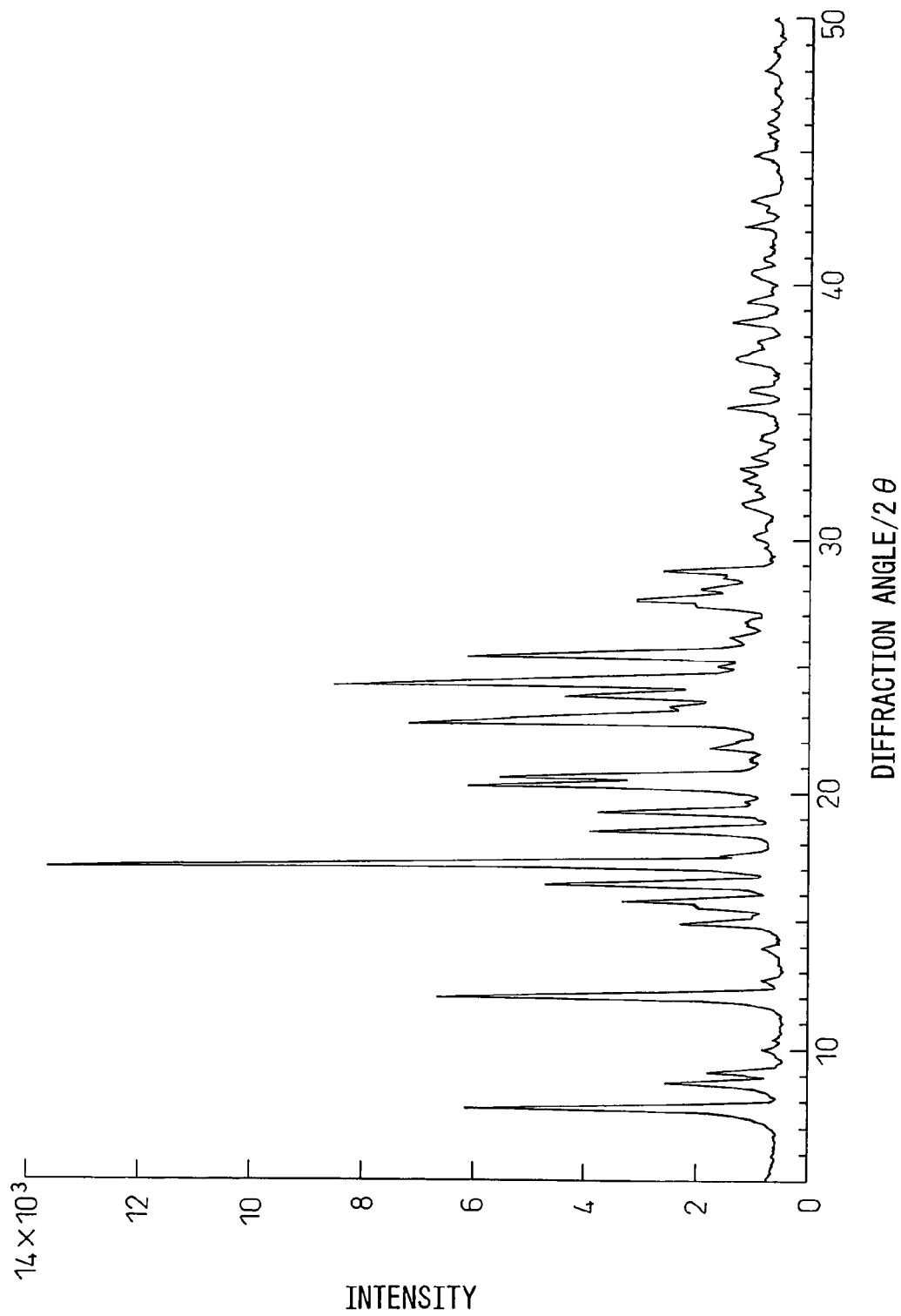
FIG. 7 is a graph showing XRD of an ethanolate crystal of the present invention.

The ethanolate crystal of the present invention yields a powder X-ray diffraction pattern at reflection angles 2θ of approximately 7.8°, 12.1°, 17.2°, 20.4°, 20.6°, 22.9°, 24.4° and 25.5° and, more specifically, it yields a powder X-ray diffraction pattern having a characteristic peak shown in Table 7 (see FIG. 7).

TABLE 7

| Ethanolate | |
|---|---|
| Diffraction angle (2θ, °) | Intensity (I/I$_{max}$*100) |
| 7.8 | 52 |
| 12.1 | 41 |
| 17.2 | 100 |
| 20.4 | 41 |
| 20.6 | 44 |
| 22.9 | 44 |
| 24.4 | 52 |
| 25.5 | 35 |

Figure 8:
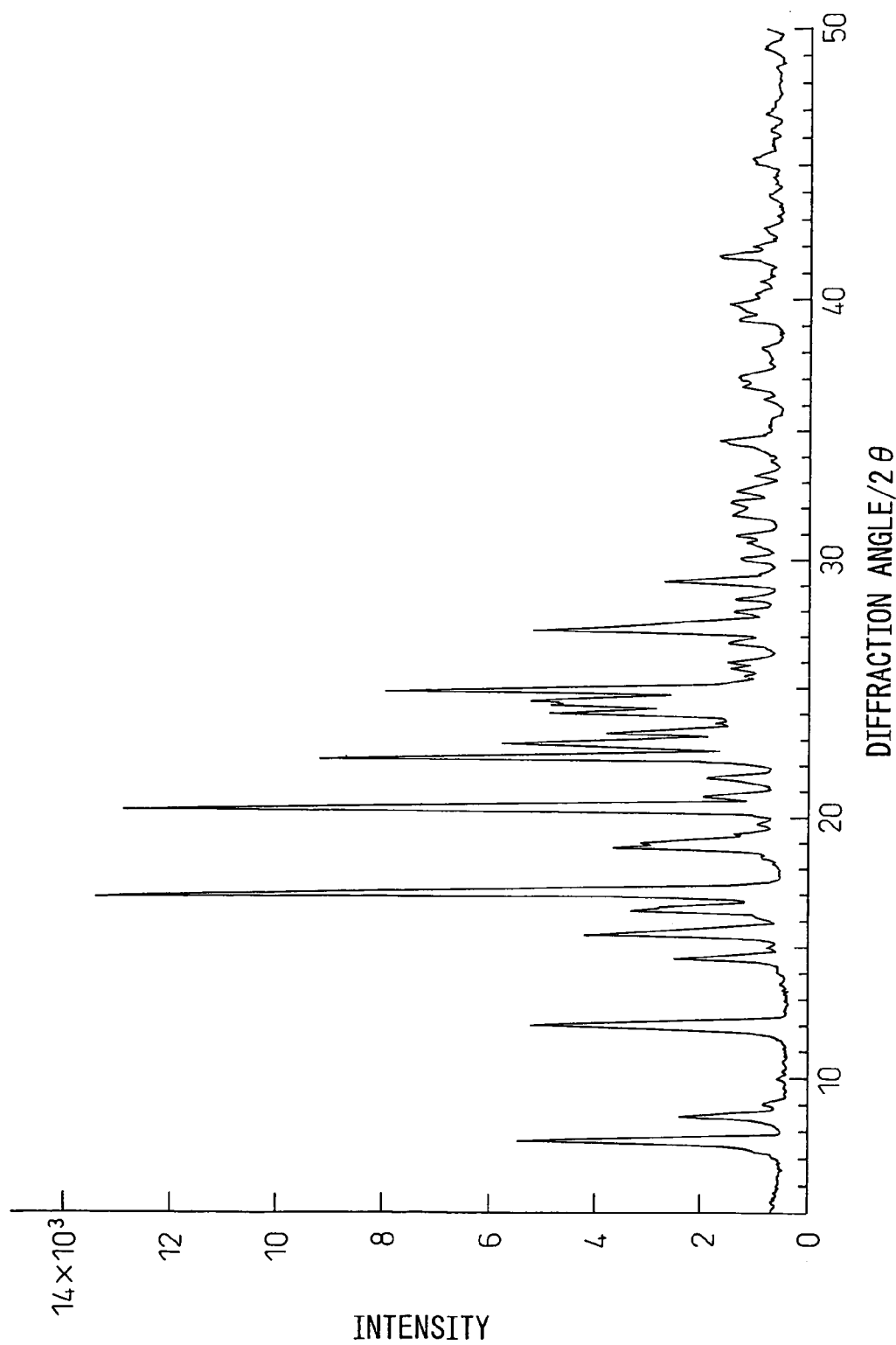
FIG. 8 is a graph showing XRD of a 1-propanolate crystal of the present invention.

The 1-propanolate crystal of the present invention yields a powder X-ray diffraction pattern at reflection angles 2θ of approximately 7.7°, 12.1°, 17.1°, 20.5°, 22.4° and 25.0° and, more specifically, it yields a powder X-ray diffraction pattern having a characteristic peak shown in Table 8 (see FIG. 8).

TABLE 8

| 1-Propanolate | |
|---|---|
| Diffraction angle (2θ, °) | Intensity (I/I$_{max}$*100) |
| 7.7 | 40 |
| 12.1 | 40 |
| 17.1 | 100 |
| 20.5 | 87 |
| 22.4 | 60 |
| 25.0 | 51 |

Figure 9:
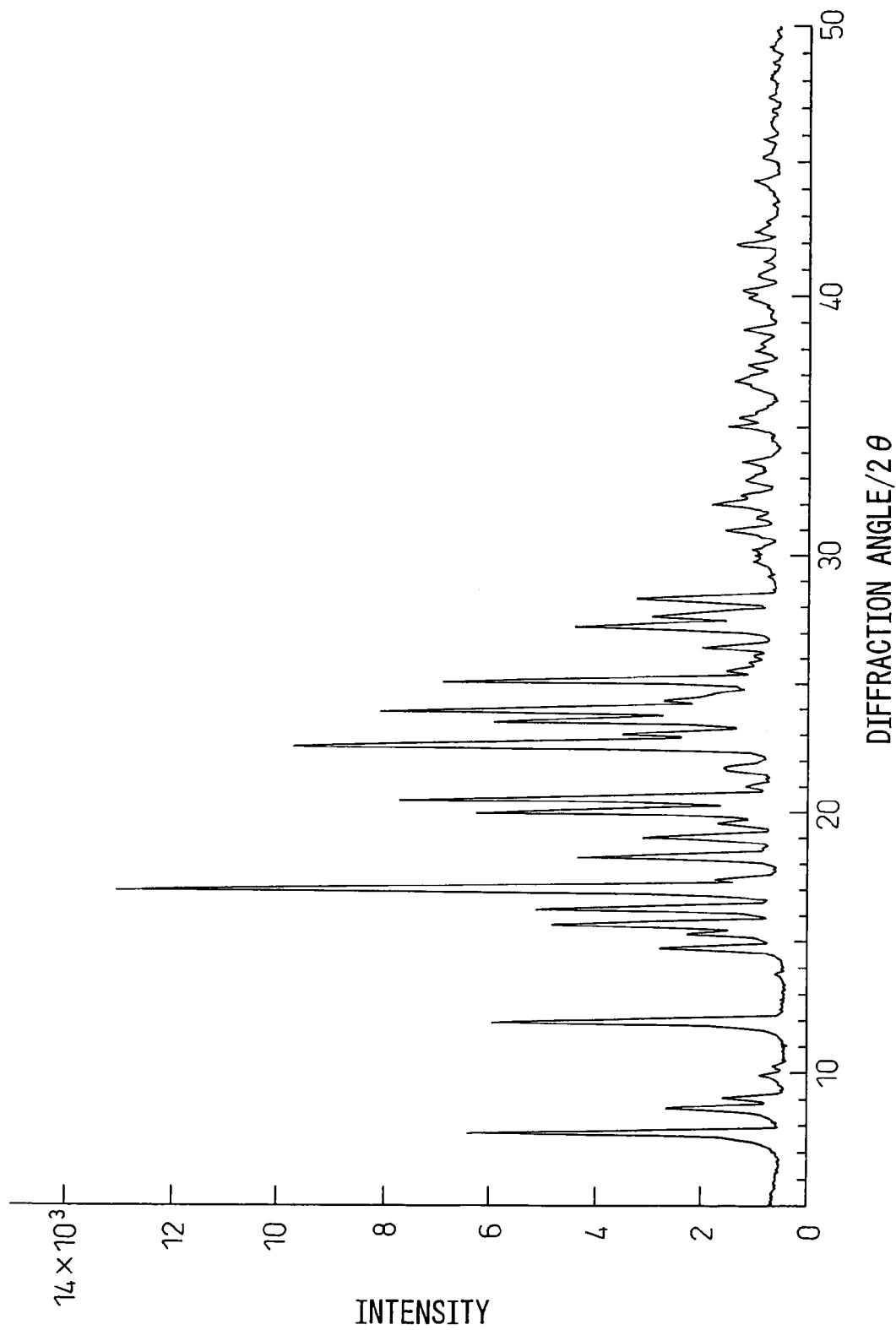
FIG. 9 is a graph showing XRD of a 2-propanolate crystal of the present invention.

The 2-propanolate crystal of the present invention yields a powder X-ray diffraction pattern at reflection angles 2θ of approximately 7.8°, 12.0°, 17.1°, 20.1°, 20.6°, 22.7°, 24.0° and 25.2° and, more specifically, it yields a powder X-ray diffraction pattern having a characteristic peak shown in Table 9 (see FIG. 9).

TABLE 9

| 2-Propanolate | |
|---|---|
| Diffraction angle (2θ, °) | Intensity (I/I$_{max}$*100) |
| 7.8 | 48 |
| 12.0 | 54 |
| 17.1 | 100 |
| 20.1 | 48 |
| 20.6 | 58 |
| 22.7 | 78 |
| 24.0 | 65 |
| 25.2 | 52 |

Figure 10:
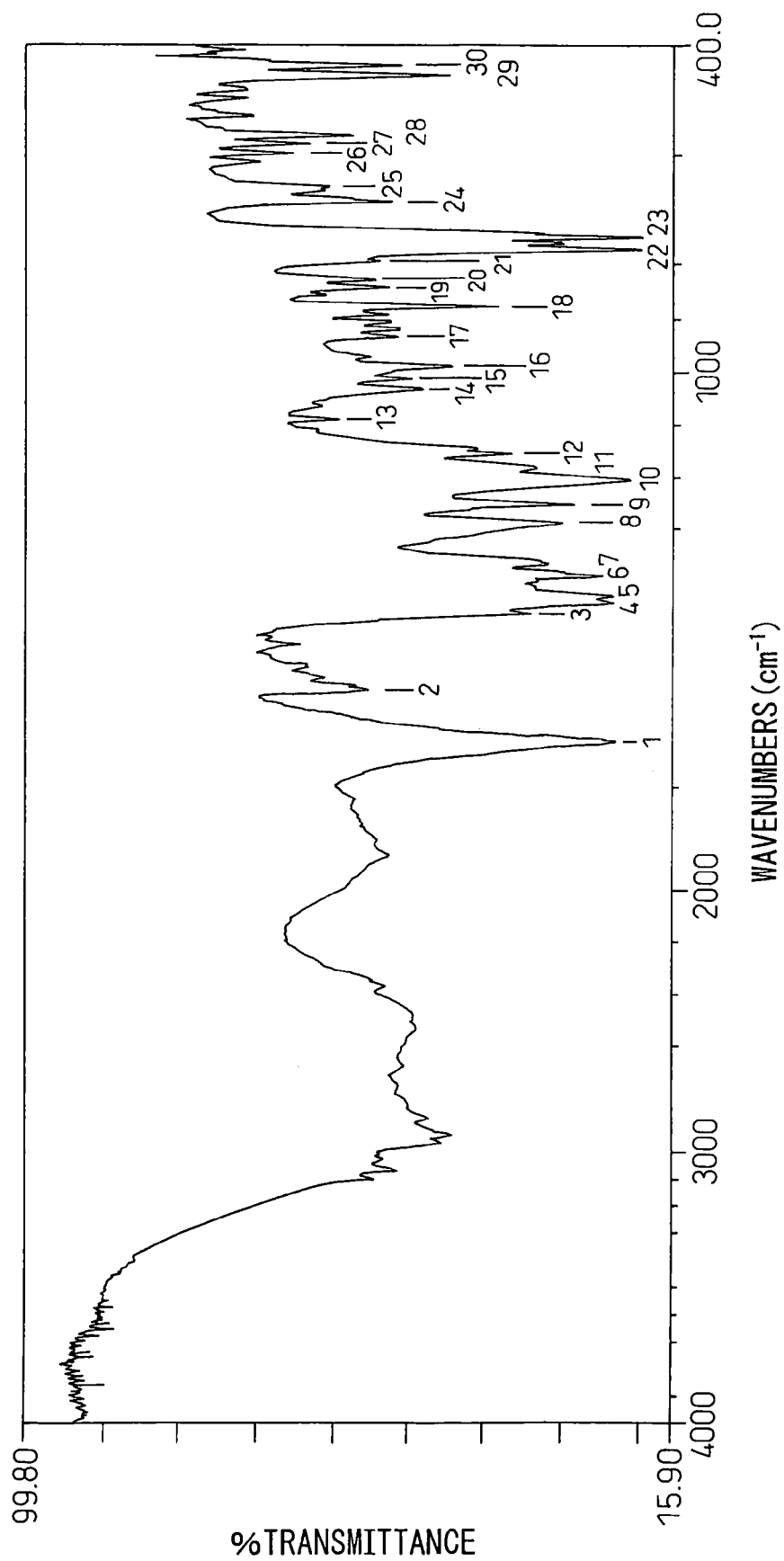
FIG. 10 is a graph showing IR of a crystal A of the present invention.

By means of infrared spectrophotometry, the crystal A of the present invention has peaks at wave numbers of approximately 1711, 1442, 1285, 1252, 1204, 771 and 750 cm$^{-1}$ (see FIG. 10).

Figure 11:
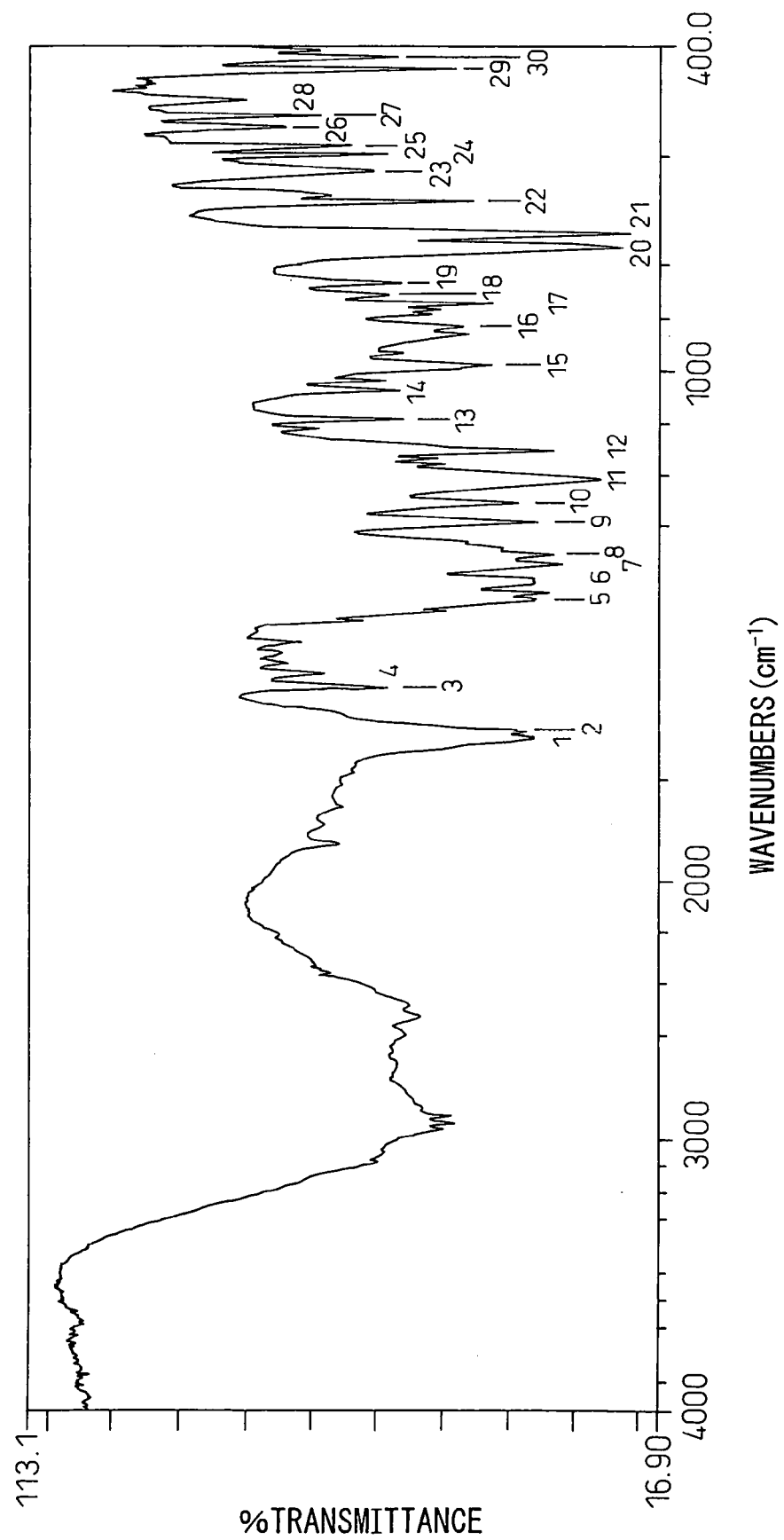
FIG. 11 is a graph showing IR of a crystal B of the present invention.

The crystal B of the present invention has peaks at wave numbers of approximately 1716, 1701, 1290, 1252, 1207, 1151, 768 and 743 cm$^{-1}$ (see FIG. 11).

Figure 12:
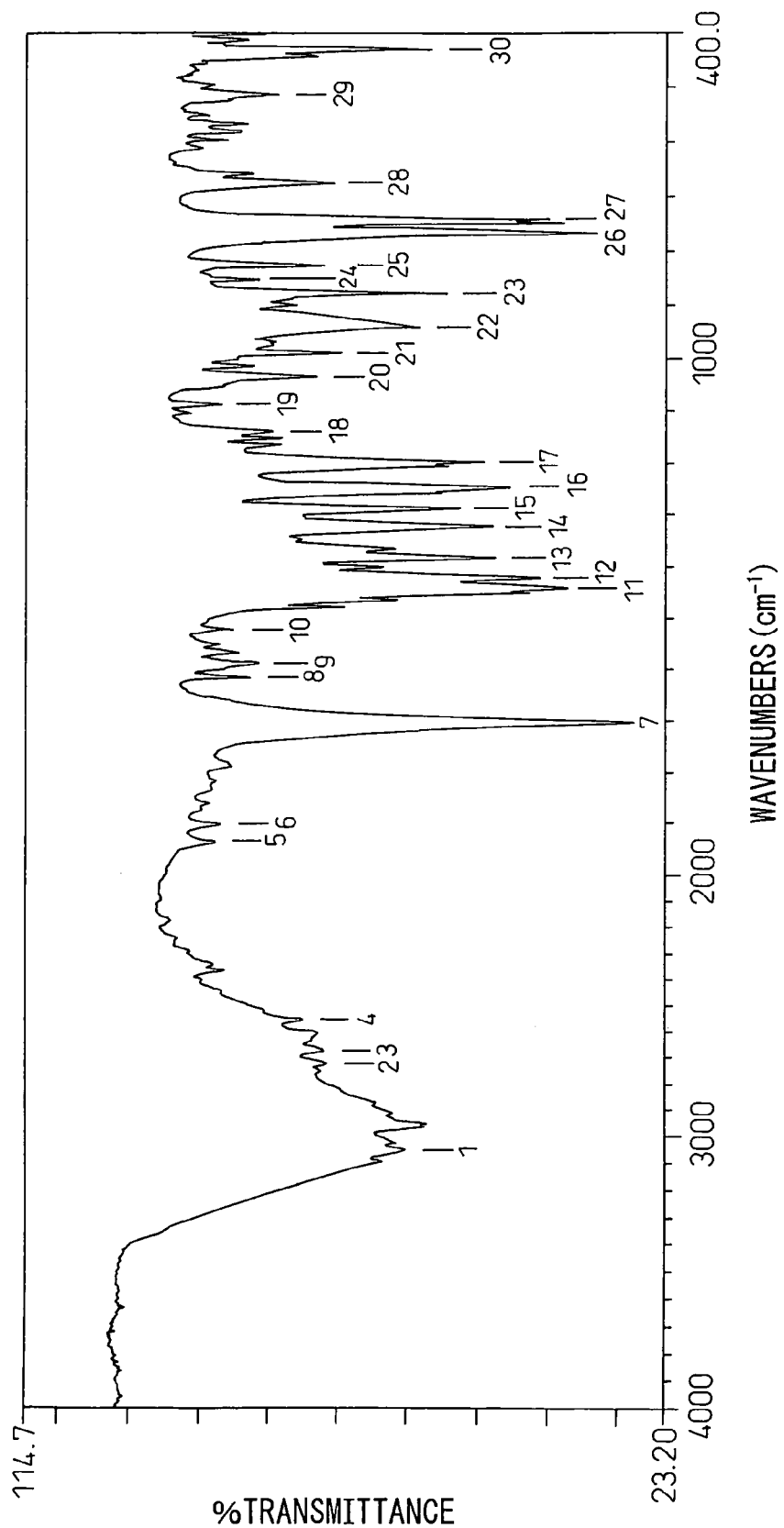
FIG. 12 is a graph showing IR of a crystal D of the present invention.

The crystal D of the present invention has peaks at wave numbers of approximately 1703, 1441, 1383, 1321, 1245, 1196, 766 and 746 cm$^{-1}$ (see FIG. 12).

Figure 13:
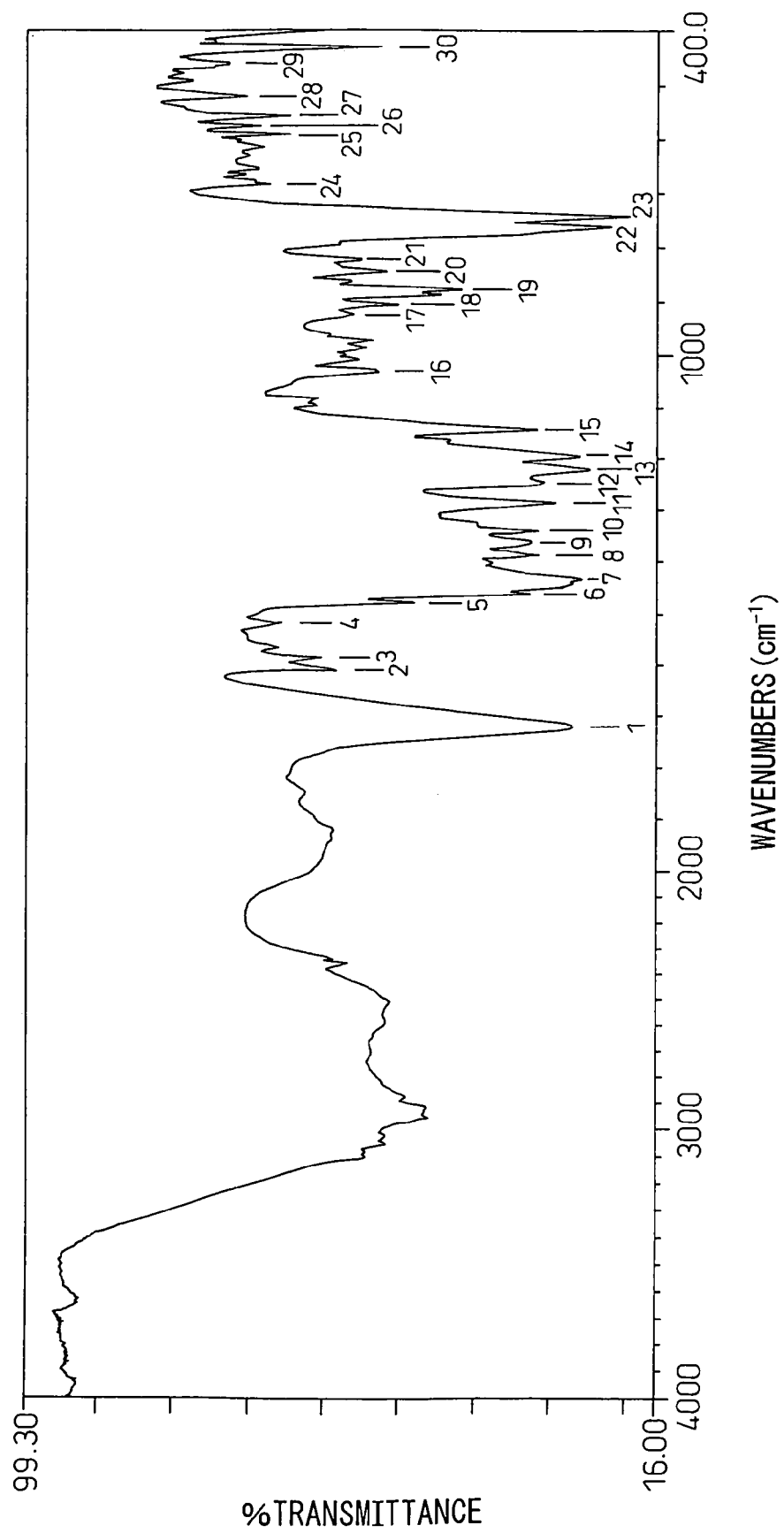
FIG. 13 is a graph showing IR of a crystal E of the present invention.

The crystal E of the present invention has peaks at wave numbers of approximately 1716, 1286, 1221, 1196, 1144, 761 and 742 cm$^{-1}$ (see FIG. 13).

Figure 14:
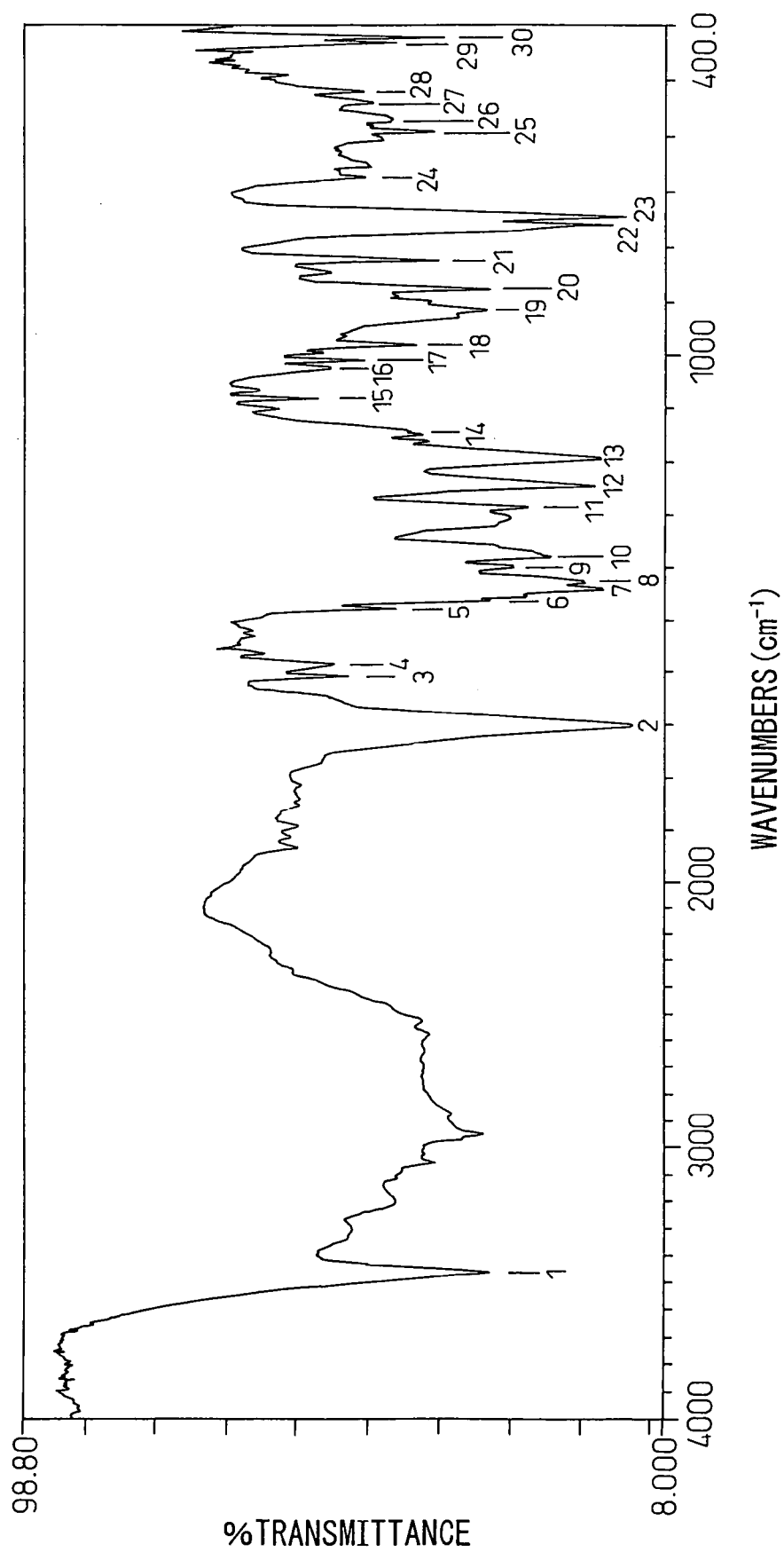
FIG. 14 is a graph showing IR of a hydrate crystal of the present invention.

The hydrate crystal of the present invention has peaks at wave numbers of approximately 1705, 1310, 1288, 1248, 1194, 760 and 746 cm$^{-1}$ (see FIG. 14).

Figure 15:
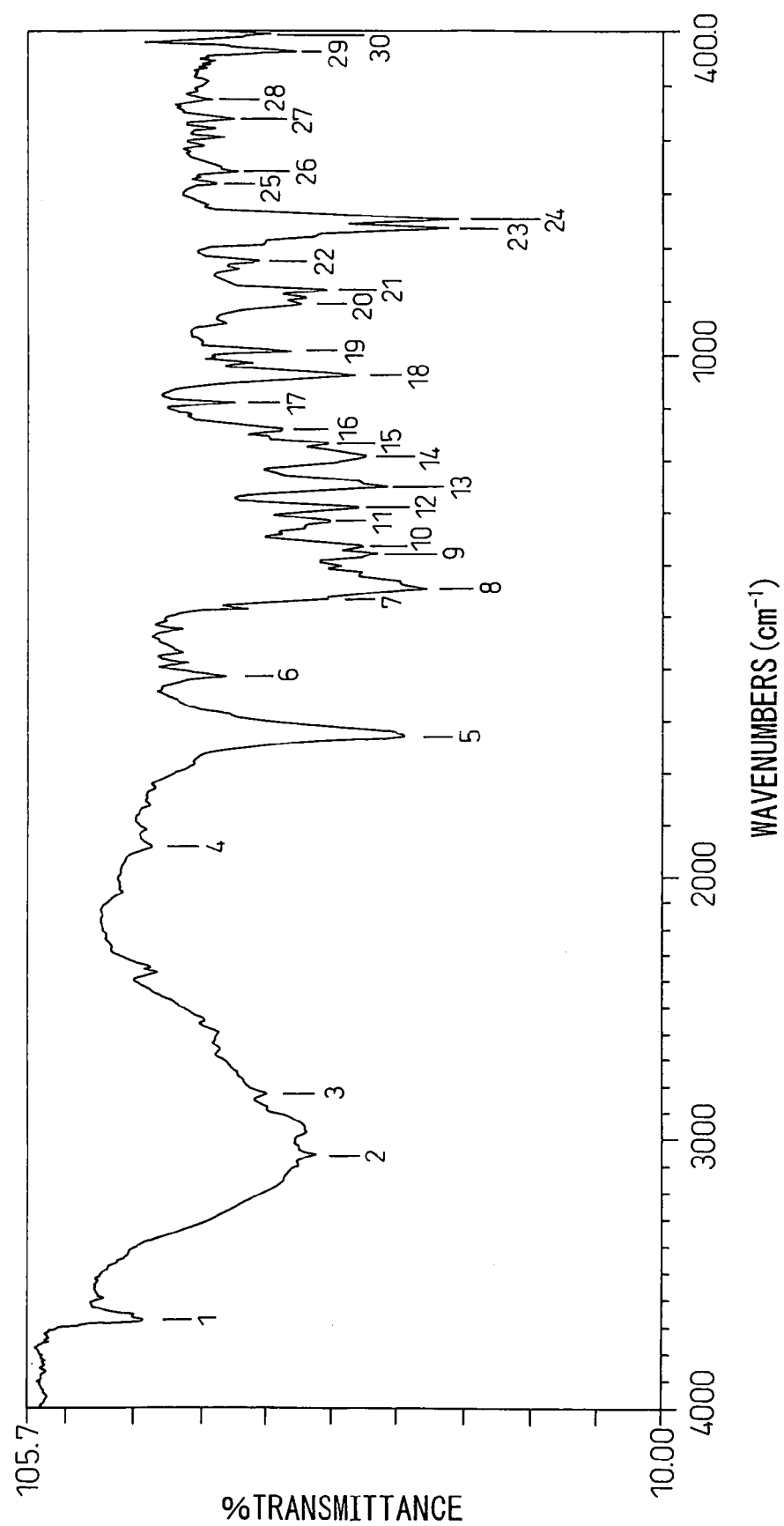
FIG. 15 is a graph showing IR of a methanolate crystal of the present invention.

The methanolate crystal of the present invention has peaks at wave numbers of approximately 1728, 1444, 1250, 1190, 1038, 764 and 748 cm$^{-1}$ (see FIG. 15).

Figure 16:
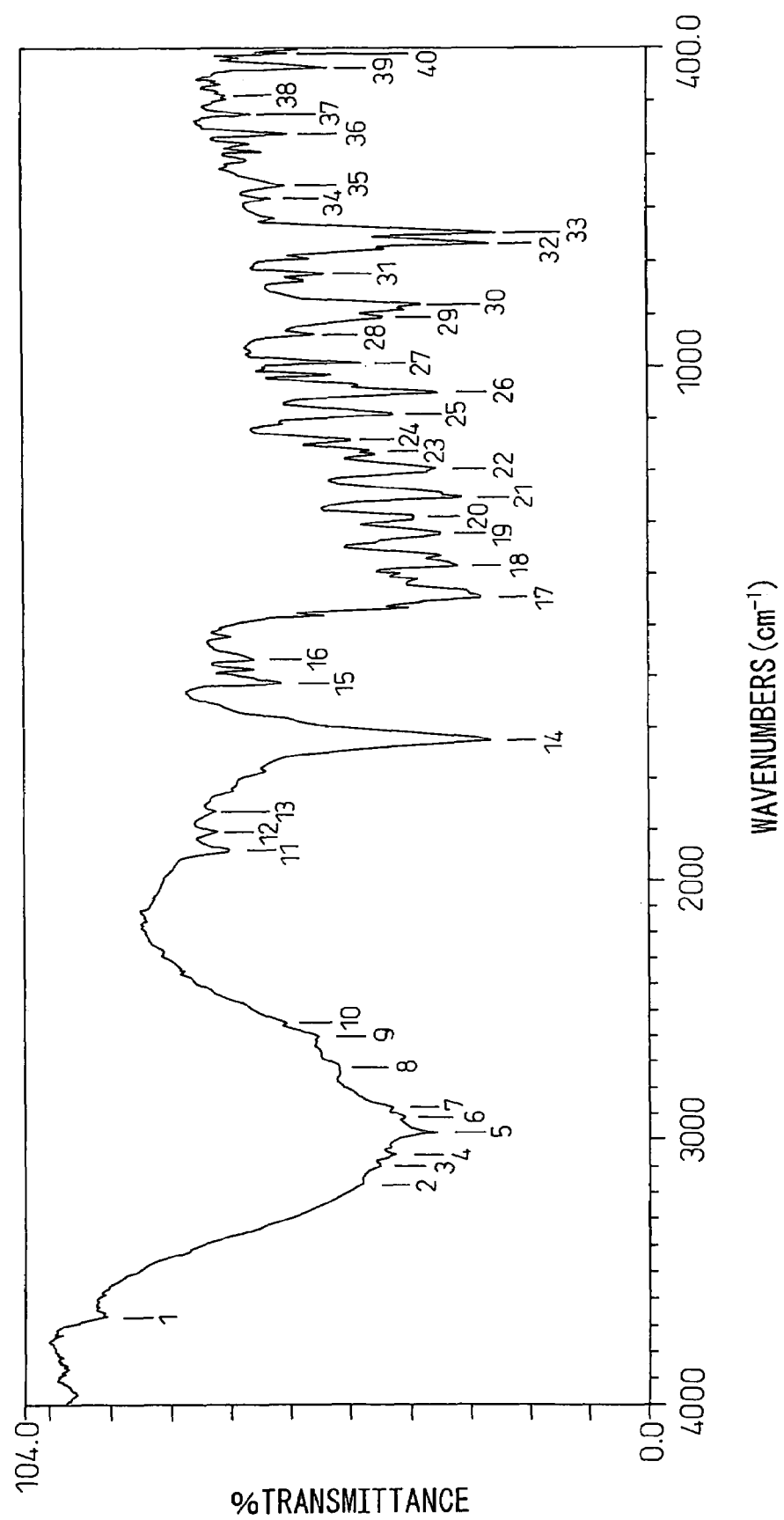
FIG. 16 is a graph showing IR of an ethanolate crystal of the present invention.

The ethanolate crystal of the present invention has peaks at wave numbers of approximately 1724, 1444, 1250, 1194, 1047, 766 and 746 cm$^{-1}$ (see FIG. 16).

Figure 17:
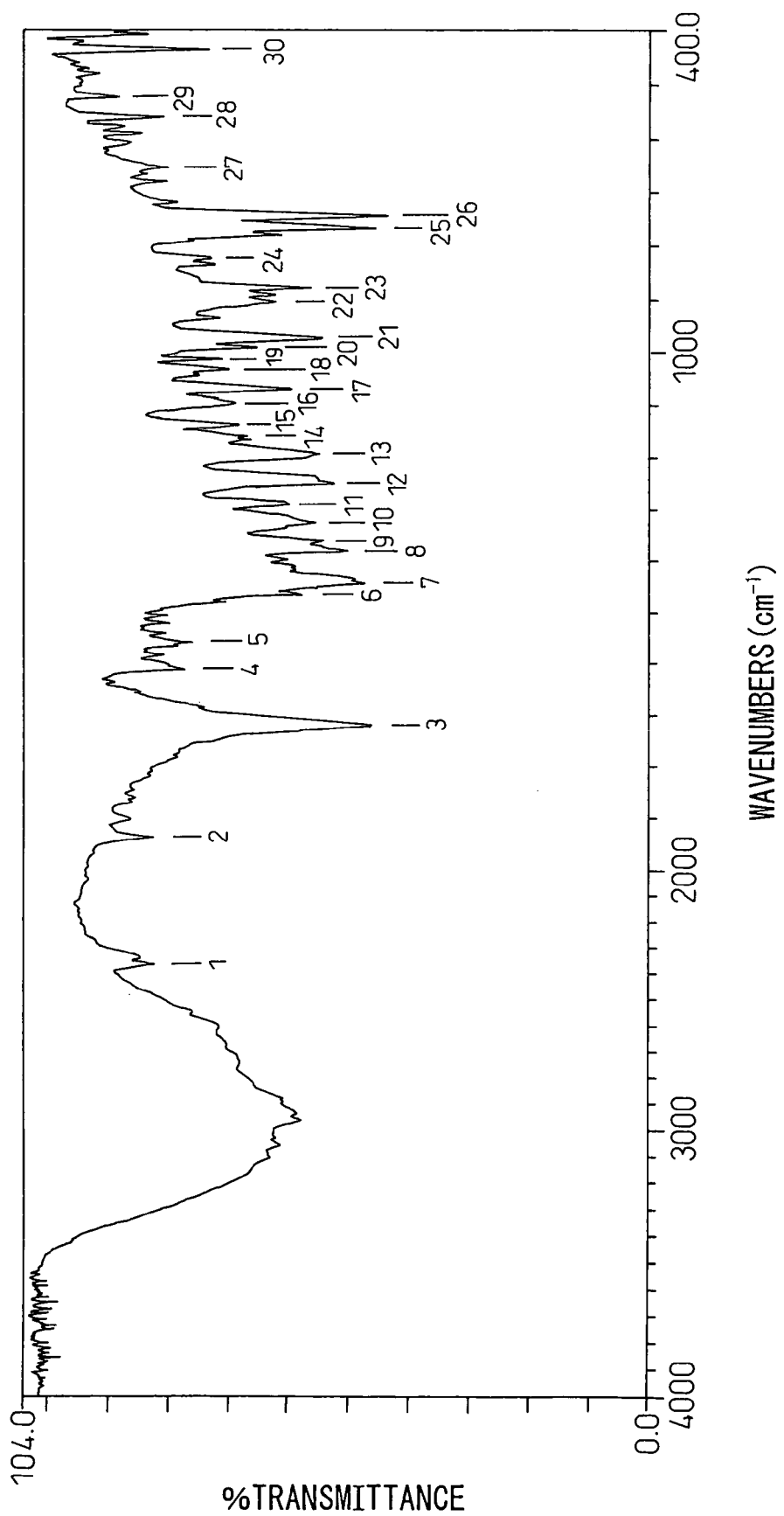
FIG. 17 is a graph showing IR of a 1-propanolate crystal of the present invention.

The 1-propanolate crystal of the present invention has peaks at wave numbers of approximately 1722, 1444, 1252, 1195, 974, 764 and 744 cm$^{-1}$ (see FIG. 17).

Figure 18:
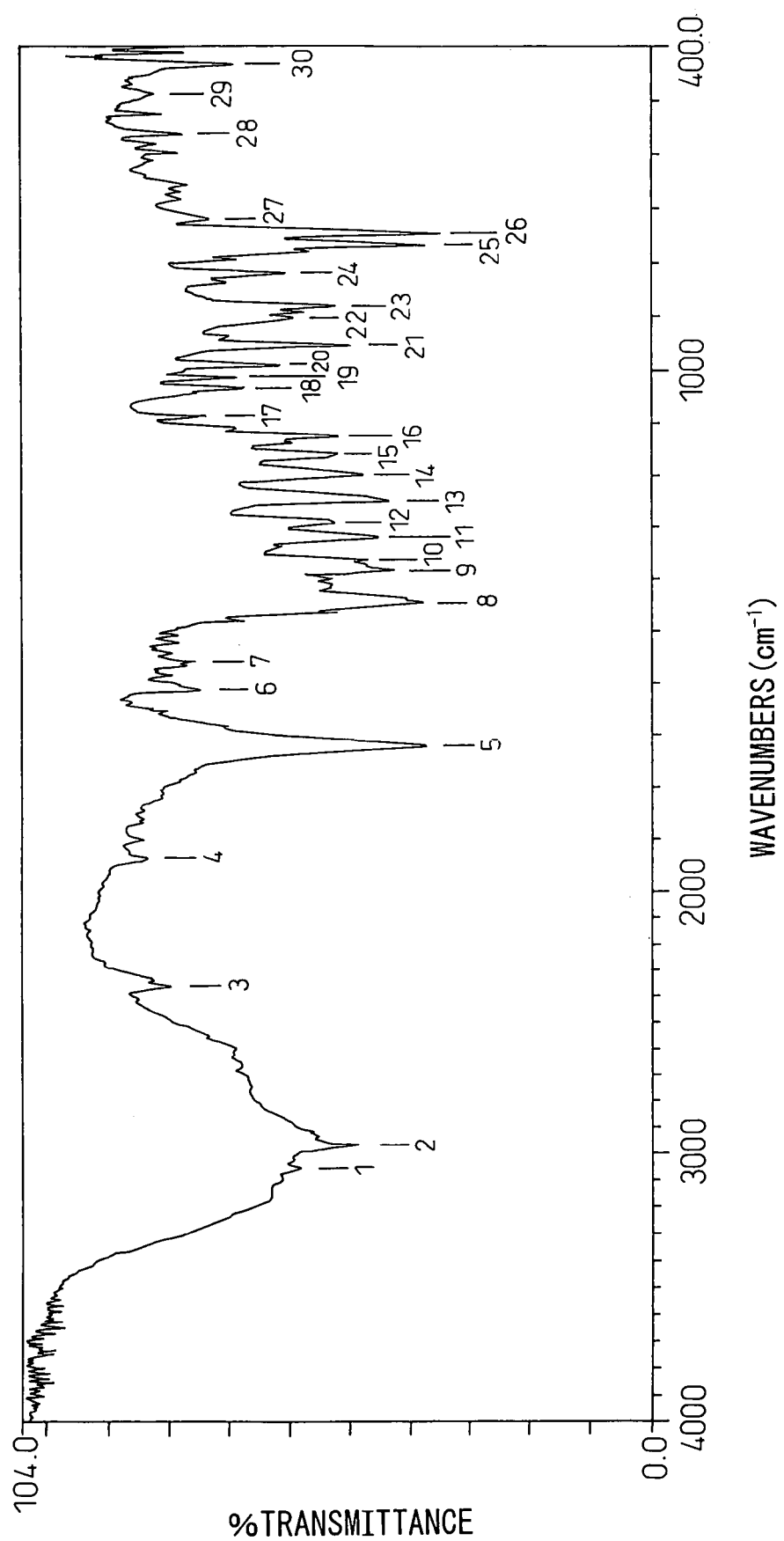
FIG. 18 is a graph showing IR of a 2-propanolate crystal of the present invention.

The 2-propanolate crystal of the present invention has peaks at wave numbers of approximately 1722, 1444, 1250, 1198, 953, 766 and 744 cm$^{-1}$ (see FIG. 18).

The wave number of the present invention by means of infrared spectrophotometry can vary by approximately 5 cm$^{-1}$ with the measuring conditions and the state of samples and the like.

The crystal of the present invention can be obtained by various processes and typical examples thereof are shown below.

The compound of the present invention, 4-(1-((4-methyl-benzothiophen-3-yl)methyl)benzimidazol-2-ylthio)butanoic acid can be synthesized by the processes described in WO 00/03997 or WO 01/53291. For example, 3-bromomethyl-4-methylbenzothiophene and methyl 4-(benzimidazol-2-ylthio)butanoate are subjected to a coupling reaction in a hydrocarbon solvent such as toluene in the presence of an alkali such as tertiary amine to obtain methyl(1-((4-methyl-benzothiophen-3-yl)methyl)benzimidazol-2-ylthio)butanoate. The resulting compound is hydrolyzed by an aqueous sodium hydroxide solution and the like in a tetrahydrofuran solvent, and then neutralized to obtain (1-((4-methylbenzothiophen-3-yl)methyl)benzimidazol-2-ylthio)butanoic acid.

The stability of four kinds of crystals excluding the solvate becomes lower in the order of crystal D, crystal B, crystal A and crystal E, while the solubility in the solvent becomes higher in this order.

The crystals A, B and D can be formed by a cooling crystallization process from a solution using various solvents, or a process for addition of a poor solvent to rich solvent solution. Examples of the solvent include acetone, anisole, ethanol, formic acid, ethyl formate, cumene, acetic acid, isobutyl acetate, isopropyl acetate, ethyl acetate, butyl acetate, propyl acetate, methyl acetate, diethyl ether, t-butylmethyl ether, 1-butanol, 2-butanol, 1-propanol, 2-propanol, heptane, 1-pentanol, 4-methyl-pentanone, 2-butanone, 3-methyl-1-butanol, 2-methyl-1-propanol, tetrahydrofuran, acetonitrile, cyclohexane, 1,2-dimethoxyethane, 1,4-dioxane, 2-ethoxyethanol, hexane, pentane, methanol, 2-ethoxymethanol, methylcyclohexane, tetralin, toluene, xylene, water, or a mixed solvent of two or more kinds selected from them. Examples of the solvent, which is preferred from economical and industrial points of views, include acetic acid, methyl acetate, ethyl acetate, propyl acetate, isopropyl acetate, butyl acetate, 4-methyl-2-pentanone, 2-butanone, acetone, tetrahydrofuran, acetonitrile, hexane, cyclohexane, heptane, toluene, xylene, methanol, ethanol, 1-propanol, 2-propanol, water, or a mixed solvent of two or more kinds selected from them. Examples of more preferred solvent include acetic acid, tetrahydrofuran, methanol, 2-butanone, water, or a mixed solvent of two or more kinds selected from them. As described hereinafter, since the alcoholate is likely to be crystallized, it is necessary to avoid the use of an alcohol having 3 or less carbon atoms such as methanol, ethanol, 1-propanol or 2-propanol as a main solvent.

In case the crystal A or B is obtained by a cooling crystallization process or a poor solvent addition process, it is preferred that the crystal D does not exist in 4-(1-((4-methylbenzothiophen-3-yl)methyl)benzimidazol-2-ylthio)butanoic acid to be used as a raw material. Since the crystal D has drastically poor solubility in the solvent, its dissolution process requires not only a large amount of the solvent and high temperature, but also a long time, and thus formation of the crystal D is accelerated and also rapid decrease of the solution temperature during filtration of an insoluble matter with heating causes acceleration of formation of the crystal D. Also transition of the crystals A or B thus obtained to the crystal D is sometimes accelerated to form the crystal D.

In case the crystal A or B is obtained by a cooling crystallization process or a poor solvent addition process, chemical purity of 4-(1-((4-methylbenzothiophen-3-yl)methyl)benzimidazol-2-ylthio)butanoic acid to be used as a raw material is deemed to be important. In case of a raw material containing a large amount of byproducts produced during the synthesis process, for example, a raw material having purity of 95% or less as measured by HPLC analysis, the crystal A is preferentially formed. In case of a raw material having comparatively high purity, for example, a raw material having purity of 97% or more as measured by HPLC analysis, the crystal B is preferentially formed. Starting material with a relatively high purity can be obtained by synthesis without forming substantial amount of byproducts, followed by purification by column chromatography or the like.

In case the crystal A, B or D is obtained by a cooling crystallization process or a poor solvent addition process, the solution temperature is not specifically limited and is preferably 40° C. or higher and lower than the boiling point of the solvent used. The amount of the solvent is not specifically limited and is preferably from 5- to 100-fold, preferably not more than 50-fold, and more preferably not more than 20-fold the amount of the raw material. As used herein, a 1-fold amount refers to an amount (1 mL) of the solvent based on 1 g of the raw material. Examples of the solvent having high solubility, which is preferably used for the purpose of decreasing the amount of the solvent, include acetic acid and tetrahydrofuran.

In case the crystal A, B or D by a cooling crystallization process, it is effective to add a seed crystal having the same crystal form as that of the objective crystal. The amount is commonly from about 0.01% to 20%, and preferably from 0.1% to 10%, based on the raw-material, and it is preferred to previously grind the seed crystal. It is necessary that the solution temperature upon addition is within a super saturated range of the crystal to be obtained.

The stirring conditions, cooling pattern and time required to collection by filtration after the starting of formation of the crystal A, B or D are not specifically limited. Since these conditions sometimes exert an influence on the yield, chemical purity, particle size and particle size distribution of the crystal, these conditions are preferably combined and set according to the purposes. In case of collection by filtration, a conventional process, for example, natural filtration, pressure filtration, filtration under reduced pressure or centrifugal separation can be employed. In case of drying, a conventional process, for example, natural drying, drying under reduced pressure, drying with heating or drying with heating under reduced pressure can be employed.

The crystal D can be obtained by adding water or nonpolar hydrocarbon as a poor solvent, to an acetic acid solution of 4-(1-((4-methylbenzothiophen-3-yl)methyl)benzimidazol-2-ylthio)butanoic acid. Examples of the nonpolar hydrocarbon include pentane, hexane, cyclohexane, heptane, or a mixed solvent of two or more kinds selected from them. The higher the temperature of the acetic acid solution used to add the poor solvent, the better because the amount of acetic acid can be reduced, thereby to improve the yield. When the amount of poor solvent is small based on the acetic acid, a cooling crystallization state sometimes arises and thus the crystal D can not be formed. The amount of the poor solvent is more than half of the amount of acetic acid, and preferably the same as or more than that of acetic acid, although it varies with the solution temperature.

The crystal B can be obtained by performing neutralization crystallization by the addition of acid to a solution of an alkali metal salt of 4-(1-((4-methylbenzothiophen-3-yl)methyl)benzimidazol-2-ylthio)butanoic acid and water, and tetrahydrofuran, methanol, 2-butanone, or a mixed solvent of two or more kinds selected from them while maintaining at about 40° C. or higher. The alkali metal is preferably sodium or potassium. The alkali metal salt is obtained by reacting (1-((4-methylbenzothiophen-3-yl)methyl)benzimidazol-2-ylthio)butanoic acid with an alkali, or hydrolyzing an ester of (1-((4-methylbenzothiophen-3-yl)methyl)benzimidazol-2-ylthio)butanoic acid and a lower alcohol. The aqueous solution may contain an organic solvent such as tetrahydrofuran, methanol or 2-butanone. The amount of water based on the alkali metal salt varies with the kind and amount of the coexisting organic solvent, and is preferably 1- to 10-fold, and preferably from 2- to 5-fold the amount of the alkali metal salt so as to ensure a solution state at the neutralization temperature. Since strong acid such as sulfuric acid or hydrochloric acid is sometimes crystallized by forming a strong acid salt of (1-((4-methylbenzothiophen-3-yl)methyl)benzimidazol-2-ylthio)butanoic acid, an organic acid such as acetic acid is preferably used for neutralization.

When the solution temperature of the salt during completion of neutralization is high, preferably about 50° C. or higher, the crystal B is formed. On the other hand, when the solution temperature is low, preferably about 40° C. or lower, the hydrate crystal is formed. Since acetic acid is also a rich solvent, the objective crystal can not be obtained sometimes in case of adding acetic acid in the amount more than that required for neutralization, and thus an attention must be paid.

The crystal E can be obtained by drying a hydrate crystal. In case of drying, a conventional drying process, for example, natural drying, drying under reduced pressure, drying with heating or drying with heating under reduced pressure can be employed. To shorten the drying time, drying under reduced pressure or drying with heating under reduced pressure is preferably employed. During drying, a mixture of the hydrate crystal and the crystal E exists.

Therefore, in case of obtaining the hydrate crystal, moderate dying conditions such as drying at room temperature under reduced pressure within a short time must be selected so that only adhesion water is removed.

The methanolate, ethanolate, 1-propanolate and 2-propanolate crystals can be obtained by cooling crystallization from a solution of a solvent containing its alcohol as a main ingredient. As the solvent, an alcohol solvent alone is most preferred and may contain another solvent as far as it is a solvent other than the other alcohol. With respect to an alcohol having 4 or more carbon atoms, a corresponding alcoholate has never been found.

Furthermore, the methanolate, ethanolate, 1-propanolate and 2-propanolate crystals can also be obtained by contacting the crystal E, the hydrate crystal or a mixture thereof with the corresponding alcohol. Specific examples of the process include a process of suspending the crystal E, the hydrate crystal or a mixture thereof in an alcohol and stirring the suspension, and a process of passing an alcohol through a container filled with the crystal E, the hydrate crystal or a mixture thereof.

Since the crystal D is a stable crystal, it can also be produced by suspending the other crystal, which is the crystal A, crystal B, crystal E, hydrate crystal, alcoholate crystal, or mixed crystal of two or more kinds selected from them, in a solvent and transiting into the crystal D (transition mediated by the solvent).

Examples of the solvent used for transition to the crystal D from the other crystal, which is mediated by the solvent, include acetone, anisole, ethanol, formic acid, ethyl formate, cumene, acetic acid, isobutyl acetate, isopropyl acetate, ethyl acetate, butyl acetate, propyl acetate, methyl acetate, diethyl ether, t-butylmethyl ether, 1-butanol, 2-butanol, 1-propanol, 2-propanol, heptane, 1-pentanol, 4-methyl-2-pentanone, 2-butanone, 3-methyl-1-butanol, 2-methyl-1-propanol, tetrahydrofuran, acetonitrile, cyclohexane, 1,2-dimethoxyethane, 1,4-dioxane, 2-ethoxyethanol, hexane, pentane, methanol, 2-ethoxymethanol, methylcyclohexane, tetralin, toluene, xylene, water, or a mixed solvent of two or more kinds selected from them. Furthermore, examples of the solvent, which is preferred from economical and industrial points of views, include acetic acid, methyl acetate, ethyl acetate, propyl acetate, isopropyl acetate, butyl acetate, 4-methyl-2-pentanone, 2-butanone, acetone, tetrahydrofuran, acetonitrile, hexane, cyclohexane, heptane, toluene, xylene, methanol, ethanol, 1-propanol, 2-propanol, water, or a mixed solvent of two or more kinds selected from them. When a mixed solvent is used, it is preferred to transit in a state where the solvents are compatible.

To shorten the time required for transition to the crystal D from the other crystal, which is mediated by the solvent, it is effective to add the crystal D as a seed crystal. The amount is commonly from about 0.01% to 20%, and preferably from 0.1% to 10% of the amount of the other crystal to be transitted, and it is preferred to previously grind the crystal. The seed crystal may be previously mixed with the raw material or added to the suspension later.

The higher the temperature during transition from the other crystal to the crystal D, which is mediated by the solvent, the more the transition rate increases. To avoid decomposition of 4-(1-((4-methylbenzothiophen-3-yl)methyl)benzimidazol-2-ylthio)butanoic acid, the temperature is preferably controlled to 100° C. or lower.

The amount of the solvent used during transition must be set so as to ensure a suspension state at the transition temperature, and is commonly from 2- to 100-fold, preferably not more than 50-fold, and more preferably not more than 20-fold the amount of the other crystal to be transited. In case the amount of the solvent is large and the amount of 4-(1-((4-methylbenzothiophen-3-yl)methyl)benzimidazol-2-ylthio) butanoic acid to be dissolved is comparatively large, the crystal other than the crystal D may be precipitated during the cooling process up to the filtration temperature even if the entire precipitated crystal is transited to the crystal D, and thus the crystal D can be precipitated by decreasing the cooling rate.

From the above-described points of view, the crystal D can be obtained by properly combining the transition temperature, the amount of the solvent and the cooling rate. It is preferred to stir because the transition rate increases.

In case of obtaining a mixture of two or more kinds of crystals as the objective product, not only the respective crystals are separately produced and mixed, but also the mixture can be produced at a time. To obtain a mixture in the objective mixing ratio, conditions must be set based on detailed preparatory study. The mixing ratio varies with the combination and ratio of the crystals and may be calculated by analysis means such as powder X-ray diffraction pattern, infrared absorption spectrum, and thermal analysis. In that case, it is considered that transition mediated by the solvent as the production process is performed comparatively easily because the mixing ratio can be successively monitored.

Although the respective crystals of the present invention can be distinguish from the other crystal form by a characteristic powder X-ray diffraction pattern or an infrared absorption spectrum, no reference is made concerning a contamination rate of the other crystal form. When a specific crystal alone is used, it is possible to permit contamination which can not be detected by its pattern or spectrum. When a specific crystal is used as a drug substance of the medicine, it is intended to permit incorporation of the other crystal.

Any crystals of the present invention can be used as an active pharmaceutical ingredients of the medicine. These crystals can be used alone or used as a mixture of two or more kinds of them.

In the present invention, the use of a crystal of 4-(1-((4-methylbenzothiophen-3-yl)methyl)benzimidazol-2-ylthio) butanoic acid or a solvate thereof is advantageous for handling, reproducibility and stability during production, and storage stability as compared with the case of using no crystal.

Particularly, the crystal D is preferably used as a stable crystal which is excellent in reproducibility and stability during production, and storage stability. The crystal A, the crystal B, the crystal E, the hydrate crystal, the methanolate crystal, the ethanolate crystal, the 1-propanolate crystal and the 2-propanolate crystal are easily handled because of their crystal forms and the purification and drying effect is easily exerted, and also these crystals are excellent in storage stability and are useful as a raw material (production intermediate) for transition into the crystal D. Furthermore, the crystal A, the crystal E and the hydrate crystal have excellent solubility in the solvent and comparatively excellent absorptivity. Since the crystal B is a metastable crystal, it is excellent in reproducibility and stability during production, and storage stability, and is also particularly useful as a raw material (production intermediate) for transition into the crystal D.

The respective crystals of 4-(1-((4-methylbenzothiophen-3-yl)methyl)benzimidazol-2-ylthio)butanoic acid or a solvate thereof of the present invention can constitute pharmaceutical compositions with pharmaceutically acceptable carriers, and be administered orally or parenterally in various dosage form. Parenterally administration includes, for example, administration by intravenous, subcutaneous, intramusclar, transdermal, intrarectal, transnasal and instillation methods.

The dosage form of the pharmaceutical composition includes, for example, tablets, pills, granules, powder, solution, suspension, syrup, or capsules, in the case of oral administration. As a method for producing a tablet, it can be formed by conventional techniques using a pharmaceutically acceptable carrier such as excipient, binder or disintegrant, etc. Also, the form of a pill, granules, or powder can be produced by the conventional techniques using excipient, etc. in the same manner as the tablet. The form of a solution, suspension or syrup can be produced by the conventional techniques using glycerol esters, alcohols, water or vegetable oils, etc. The form of capsule can be produced by filling a capsule made of gelatine, etc. with the granules, powder or a solution, etc. Among the agents for parenteral administration, in the case of intravenous, subcutaneous or intramuscular administration, it can be administered as injection. An injection can be produced by dissolving the crystal of 4-(1-((4-methylbenzothiophen-3-yl)methyl)benzimidazol-2-ylthio)butanoic acid of the present invention in water soluble solutions such as physiological saline, or water insoluble solutions consisting of organic esters such as propylene glycol, polyethylene glycol, or vegetable oils, etc. In the case of transdermal administration, for example, a dosage form as an ointment or a cream can be employed. The ointment can be produced by mixing the crystal of the present invention with fats and oils or vaselhines, etc., and the cream can be produced by mixing a benzoic acid derivative with emulsifiers. In the case of rectal administration, it may be in the form of suppository using a gelatine soft capsule, etc. In the case of transnasal administration, it can be used as a formulation consisting of a liquid or powdery composition. As a base of a liquid formulation, water, salt solution, phosphate buffer, or acetate buffer, etc. are used, and also it may contain surfactants, antioxidants, stabilizers, preservatives, or tackifiers. A base of powdery formulation may include water-absorbing materials such as highly water-soluble polyacrylates, cellulose low-alkyl ethers, polyethylene glycol polyvinyl pyrrolidone, amylose or pullulan, etc., or water-unabsorbing materials such as, for example, celluloses, starches, proteins, gums or cross-linked vinyl polymers. The water-absorbing materials are preferable. These materials may be mixed for use. Further, antioxidants, colorants, conservatives, preservatives or, antiseptic etc. may be added to the powdery formulation. The liquid or powdery formulation can administrated using a spray apparatus. In the case of eye drop administration, an aqueous or non-aqueous eye drop can be employed. In the aqueous eye drop, as a solvent, sterilized and purified water or physiological saline, etc. can be used. When only the sterilized and purified water is employed as a solvent, an aqueous suspended eye drop can be formed by adding a suspension such as surfactants or high-molecular tackifiers, or a soluble eye drop by adding solubilizers such as nonionic surfactants. In the non-aqueous eye drop, a non-aqueous suspended eye drop can be formed by using injectable non-aqueous solvents as a solvent. In the case of administering through the eyes by means other than eye drops, the dosage form such as eye-ointments, applicating solutions, diffusing agents or insert agents can be used. Further, in the case of the inhalation through nose or mouth, a solution or suspension containing the respective crystals of 4-(1-((4-methylbenzothiophen-3-yl)methyl)benzimidazol-2-ylthio)butanoic acid of the present invention and a pharmaceutical excipient which is generally used is inhaled through an inhalant aerosol spray, etc. Also, the respective crystals of 4-(1-((4-methylbenzothiophen-3-yl)methyl)benzimidazol-2-ylthio)butanoic acid of the present invention which are in the form of dry powder can be administered through inhalator, etc. which contacts directly with lung. To these formulations, if necessary, pharmaceutically acceptable carriers such as isotonic agents, preservatives, conservatives, wetting agents, buffers, emulsifiers, dispersions or stabilizers, etc. may be added. Also, if necessary, these formulations can be sterilized by the addition of a sterilant, filtration using a bacteria-retaining filter, or treatment with heat or irradiation, etc. Alternatively, it is possible to produce an aseptic solid formulation, which can be used to be dissolved or suspended in a suitable aseptic solution immediately before use.

The dose of the crystal of 4-(1-((4-methylbenzothiophen-3-yl)methyl)benzimidazol-2-ylthio)butanoic acid of the invention varies depending on kinds of disease, route of administration, or condition, age, sex or weight of the patient, etc., but generally, is about 1-500 mg/day/human body, preferably 10-300 mg/day/human body in the case of oral administration, while is about 0.1-100 mg/day/human body, preferably 0.3-30 mg/day/human body in the case of intravenous, subcutaneous, intramuscle, transdermal, intrarectal, transnasal, instillation or inhalation.

When the crystal of 4-(1-((4-methylbenzothiophen-3-yl)methyl)benzimidazol-2-ylthio)butanoic acid of the present invention is used as a preventive, it can be administered according to well-known processes, depending on the respective conditions.

Examples of the object disease of the preventive and/or remedy of the present invention include respiratory tract diseases such as bronchial asthma; inflammatory and/or allergic diseases such as allergic rhinitis, atopic dermatitis, and urticaria; circulatory diseases such as sclerosing vascular lesion, intravascular stricture, peripheral circulatory disturbance, renal insufficiency, and cardiac insufficiency; and bone and/or cartilage metabolism diseases such as rheumatism and osteoarthritis.

EXAMPLES

The process for producing the crystal of the present invention will be illustrated using the following examples. However, the scope of the invention is not restricted in any means by these examples.

The crystal of the present invention was analyzed under the following conditions.

Conditions for Measurement of Powder X-Ray Diffraction Pattern

Apparatus: RIGAKU ROTAFLEX RU300 (powder X-ray diffractometer)

X-ray source: Cu-Kα (λ=1.5418 Å), 50 kV-200 mA

Slit: DS1°-SS1°-RS0.15 mm-graphite monochrometer-0.45 mm

Method: 2θ-θ scan, 0.05 step/sec, scan range of 5 to 80°

Conditions for Measurement of Infrared Absorption Spectrum

Apparatus: HORIBA FT-270

An infrared absorption spectrum was measured by FT-IR (Resolution: 4, SCAN: 40, Gain: AUTO) in accordance with a potassium bromide method.

Conditions of Differential Scanning Calorimetry (DSC)

Apparatus: Shimazu

Differential scanning calorimeter: DSC-50

Termal analysis system: TA-50

Reference: empty

Scan speed: 10° C./min.

Sampling: 0.5 seconds

Upper limit: 230° C.

Lower limit: 30° C.

Atmosphere: $N_2$

Sample pan: aluminum (sealed)

Sample amount: 1 to 3 mg

Although each crystal of the present invention can be specified by DSC, the value of DSC vary sometimes with the measuring conditions and sample conditions and the value of DSC shown in examples can not be specified as an absolute numerical value.

Example 1

Production of Crystal A of 4-(1-((4-methylbenzothiophen-3-yl)methyl)benzimidazol-2-ylthio)butanoic acid To 10 g of 4-(1-((4-methylbenzothiophen-3-yl)methyl)benzimidazol-2-ylthio)butanoic acid (purity: 93% measured by HPLC analysis), 50 mL of butyl acetate was added and, after heating at reflux in an oil bath, an insoluble matter was removed by filtration with heating. Dissolution was confirmed by heating at reflux again and the solution was cooled at a rate of about 40° C./hour while stirring in an oil bath. Crystallization set in at the inner temperature of about 90° C. After cooling to 20° C., the crystal was collected by filtration and then dried under reduced pressure at 60° C. for 4 hours. XRD and IR revealed that the resulting crystal is a crystal A. The yield was 75%. The melting peak temperature measured by DSC was 160° C.

Example 2

Production of Crystal B of 4-(1-((4-methylbenzothiophen-3-yl)methyl)benzimidazol-2-ylthio)butanoic acid To 10 g of 4-(1-((4-methylbenzothiophen-3-yl)methyl)benzimidazol-2-ylthio)butanoic acid (purity: 99% measured by HPLC analysis) purified by column chromatography, 100 mL of butyl acetate was added and, after heating at reflux in an oil bath, an insoluble matter was removed by filtration with heating. Dissolution was confirmed by heating at reflux again and the solution was cooled at a rate of about 20° C./hour while stirring in an oil bath. Crystallization set in at the inner temperature of about 100° C. After cooling to room temperature, the crystal was collected by filtration and then dried under reduced pressure at 60° C. for 4 hours. XRD and IR revealed that the resulting crystal is a crystal B. The yield was 70%. The melting peak temperature measured by DSC was 160° C.

Example 3

Production of Crystal B of 4-(1-((4-methylbenzothiophen-3-yl)methyl)benzimidazol-2-ylthio)butanoic acid To 10 g of 4-(1-((4-methylbenzothiophen-3-yl)methyl)benzimidazol-2-ylthio)butanoic acid, 60 mL of acetic acid and 60 mL of 2-butanone were added and, after heating again in an oil bath and dissolving at the inner temperature of 90° C., an insoluble matter was removed by filtration with heating. Dissolution was confirmed at the inner temperature of 80° C. by heating again and the solution was cooled at a rate of about 20° C./hour while stirring in an oil bath. Crystallization set in at the inner temperature of about 40° C. After cooling to 0° C., the crystal was collected by filtration and then dried under reduced pressure at 80° C. for 4 hours. XRD and IR revealed that the resulting crystal is a crystal B. The yield was 65%. The melting peak temperature measured by DSC was 161° C.

Example 4

Production of Crystal B of 4-(1-((4-methylbenzothiophen-3-yl)methyl)benzimidazol-2-ylthio)butanoic acid To 10 g of 4-(1-((4-methylbenzothiophen-3-yl)methyl)benzimidazol-2-ylthio)butanoic acid, 60 mL of acetic acid and 60 mL of 2-butanone were added and, after heating in an oil bath and dissolving at the inner temperature of 90° C., an insoluble matter was removed by filtration with heating. Dissolution was confirmed at the inner temperature of 80° C. by heating again and the solution was cooled while stirring in an oil bath. At the inner temperature of 40° C., 10 mg of crystal B of 4-(1-((4-methylbenzothiophen-3-yl)methyl)benzimidazol-2-ylthio)butanoic acid was added, thereby to accelerate crystallization. After cooling to 0° C. at a rate of about 20° C./hour, the crystal was collected by filtration and then dried under reduced pressure at 60° C. for 4 hours. XRD and IR revealed that the resulting crystal is a crystal B. The yield was 85%. The melting peak temperature measured by DSC was 159° C.

Example 5

Production of Crystal D of 4-(1-((4-methylbenzothiophen-3-yl)methyl)benzimidazol-2-ylthio)butanoic acid To 10 g of 4-(1-((4-methylbenzothiophen-3-yl)methyl)benzimidazol-2-ylthio)butanoic acid, 60 mL of acetic acid and 60 mL of 2-butanone were added and, after heating in an oil bath and dissolving at the inner temperature of 90° C., an insoluble matter was removed by filtration with heating. Dissolution was confirmed at the inner temperature of 80° C. by heating again and the solution was cooled while stirring in an oil bath. At the inner temperature of 50° C., 10 mg of crystal D of 4-(1-((4-methylbenzothiophen-3-yl)methyl)benzimidazol-2-ylthio)butanoic acid was added, thereby to accelerate crystallization. After cooling to 0° C. at a rate of about 20° C./hour, the crystal was collected by filtration and then dried under reduced pressure at 60° C. for 4 hours. XRD and IR revealed that the resulting crystal is a crystal D. The yield was 85%. The melting peak temperature measured by DSC was 180° C.

Example 6

Production of Crystal D of 4-(1-((4-methylbenzothiophen-3-yl)methyl)benzimidazol-2-ylthio)butanoic acid To 10 g of 4-(1-((4-methylbenzothiophen-3-yl)methyl)benzimidazol-2-ylthio)butanoic acid, 60 mL of acetic acid was added and, after heating in an oil bath and dissolving at the inner temperature of 95° C., an insoluble matter was removed by filtration with heating. Dissolution was confirmed at the inner temperature of 90° C. by heating again and the solution was cooled while stirring in an oil bath, and then 60 mL of water was added at the inner temperature of about 60° C., thereby to crystallize the solution. After cooling to 20° C. at a rate of about 40° C./hour, the crystal was collected by filtration and then dried under reduced pressure at 60° C. for 4 hours. XRD and IR revealed that the resulting crystal is a crystal D. The yield was 90%. The melting peak temperature measured by DSC was 178° C.

Example 7

Production of Crystal B of 4-(1-((4-methylbenzothiophen-3-yl)methyl)benzimidazol-2-ylthio)butanoic acid To 10 g of a methyl ester of 4-(1-((4-methylbenzothiophen-3-yl)methyl)benzimidazol-2-ylthio)butanoic acid, 20 mL of tetrahydrofuran and 50 mL of an aqueous 1 mol/L sodium hydroxide solution were added and, after heating again in an oil bath, the hydrolysis reaction was performed at the inner temperature of 60° C. An insoluble matter was removed by filtration with heating, and then 5 mL of acetic acid was added while maintaining the inner temperature at 60° C. After cooling to 20° C. at a rate of about 40° C./hour while stirring in an oil bath, the crystal was collected by filtration and then dried under reduced pressure at 80° C. for 4 hours. XRD and IR revealed that the resulting crystal is a crystal B. The yield was 95%. The melting peak temperature measured by DSC was 160° C.

Example 8

Production of Hydrate Crystal of 4-(1-((4-methylbenzothiophen-3-yl)methyl)benzimidazol-2-ylthio)butanoic acid To 10 g of a methyl ester of 4-(1-((4-methylbenzothiophen-3-yl)methyl)benzimidazol-2-ylthio)butanoic acid, 20 mL of tetrahydrofuran and 50 mL of an aqueous 1 mol/L sodium hydroxide solution were added and, after heating again in an oil bath, the hydrolysis reaction was performed at the inner temperature of 40° C. An insoluble matter was removed by filtration with heating, and then 5 mL of acetic acid was added while maintaining the inner temperature at 30° C. After cooling to room temperature at a rate of about 40° C./hour while stirring in an oil bath, the crystal was collected by filtration and then dried under reduced pressure at 20° C. for one hour. XRD and IR revealed that the resulting crystal is a hydrate crystal. The yield was 92%. The melting peak temperature measured by DSC was 158° C.

Example 9

Production of Crystal E of 4-(1-((4-methylbenzothiophen-3-yl)methyl)benzimidazol-2-ylthio)butanoic acid 5 g of a hydrate crystal of 4-(1-((4-methylbenzothiophen-3-yl)methyl)benzimidazol-2-ylthio)butanoic acid obtained in Example 8 was taken in a petri dish and then dried under reduced pressure at 80° C. for 8 hours. XRD and IR revealed that the resulting crystal is a crystal E. The melting peak temperature measured by DSC was 159° C.

Example 10

Production of Methanolate Crystal of 4-(1-((4-methylbenzothiophen-3-yl)methyl)benzimidazol-2-ylthio)butanoic acid To 5 g of 4-(1-((4-methylbenzothiophen-3-yl)methyl)benzimidazol-2-ylthio)butanoic acid, 100 mL of methanol was added and, after heating at reflux in an oil bath and dissolving, an insoluble matter was removed by filtration with heating. Dissolution was confirmed by heating at reflux again and the solution was cooled at a rate of about 20° C./hour while stirring in an oil bath. Crystallization set in at the inner temperature of about 30° C. After cooling to 0° C., the crystal was collected by filtration and then dried under reduced pressure at 20° C. for 1 hour. XRD and IR revealed that the resulting crystal is a methanolate crystal. The yield was 60%.

Example 11

Production of Methanolate Crystal of 4-(1-((4-methylbenzothiophen-3-yl)methyl)benzimidazol-2-ylthio)butanoic acid 2 g of a crystal E of 4-(1-((4-methylbenzothiophen-3-yl)methyl)benzimidazol-2-ylthio)butanoic acid obtained in Example 9 was suspended in 10 mL of methanol, followed by stirring at 20° C. for one hour. The crystal was collected by filtration and then dried under reduced pressure at 20° C. for 1 hour. XRD and IR revealed that the resulting crystal is a methanolate crystal. The yield was 90%.

Example 12

Production of Ethanolate Crystal of 4-(1-((4-methylbenzothiophen-3-yl)methyl)benzimidazole-2-ylthio)butanoic acid To 5 g of 4-(1-((4-methylbenzothiophen-3-yl)methyl)benzimidazole-2-ylthio)butanoic acid, 90 mL of ethanol and 10 mL of butyl acetate were added and, after heating at reflux in an oil bath and dissolving, an insoluble matter was removed by filtration with heating. Dissolution was confirmed by heating at reflux again and the solution was cooled at a rate of about 20° C./hour while stirring in an oil bath. Crystallization set in at the inner temperature of about 40° C. After cooling to 0° C., the crystal was collected by filtration and then dried under reduced pressure at 20° C. for an hour. XRD and IR revealed that resulting crystal is a ethanolate crystal. The yield was 72%.

Example 13

Production of Ethanolate Crystal of 4-(1-((4-methylbenzothiophen-3-yl)methyl)benzimidazole-2-ylthio)butanoic acid 2 g of a hydrate crystal of 4-(1-((4-methylbenzothiophen-3-yl)methyl)benzimidazole-2-ylthio)butanoic acid obtained in Example 8 was suspended in 10 mL of ethanol, followed by stirring at 30° C. for 5 hours. The crystal was collected by filtration and then dried under reduced pressure at 20° C. for an hour. XRD and IR revealed that resulting crystal is an ethanolate crystal. The yield was 88%.

Example 14

Production of 1-propanolate crystal of 4-(1-((4-methylbenzothiophen-3-yl methyl)benzimidazole-2-ylthio)butanoic acid To 5 g of 4-(1-((4-methylbenzothiophen-3-yl)methyl)benzimidazole-2-ylthio)butanoic acid, 80 mL of 1-propanol and 20 mL of 2-butanone were added and, after heating at reflux in an oil bath and dissolving, an insoluble matter was removed by filtration with heating. Dissolution was confirmed by heating at reflux again and the solution was cooled at a rate of about 20° C./hour while stirring in an oil bath. Crystallization set in at the inner temperature of about 40° C. After cooling to 0° C., the crystal was collected by filtration and then dried under reduced pressure at 20° C. for an hour. XRD and IR revealed that resulting crystal is a 1-propanolate crystal. The yield was 76%.

Example 15

Production of 1-propanolate crystal of 4-(1-((4-methylbenzothiophen-3-yl)methyl)benzimidazole-2-ylthio)butanoic acid 2 g of a hydrate crystal of 4-(1-((4-methylbenzothiophen-3-yl)methyl)benzimidazole-2-ylthio)butanoic acid obtained in Example 8 was suspended in a 9 mL of 1-propanol and 1 mL of water, followed by stirring at 30° C. for 8 hours. The crystal was collected by filtration and then dried under reduced pressure at 30° C. for an hour. XRD and IR revealed that resulting crystal is a 1-propanolate crystal. The yield was 91%.

Example 16

Production of 2-propanolate crystal of 4-(1-((4-methylbenzothiophen-3-yl)methyl)benzimidazole-2-ylthio)butanoic acid To 5 g of 4-(1-((4-methylbenzothiophen-3-yl)methyl)benzimidazole-2-ylthio)butanoic acid, 90 mL of 2-propanol and 10 mL of water were added and, after heating at reflux in an oil bath and dissolving, an insoluble matter was removed by filtration with heating. Dissolution was confirmed by heating at reflux again and the solution was cooled at a rate of about 20° C./hour while stirring in an oil bath. Crystallization set in at the inner temperature of about 50° C. After cooling to 0° C., the crystal was collected by filtration and then dried under reduced pressure at 30° C. for an hour. XRD and IR revealed that resulting crystal is a 2-propanolate crystal. The yield was 82%.

Example 17

Production of 2-propanolate crystal of 4-(1-((4-methylbenzothiophen-3-yl)methyl)benzimidazole-2-ylthio)butanoic acid 2 g of a crystal E of 4-(1-((4-methylbenzothiophen-3-yl)methyl)benzimidazole-2-ylthio)butanoic acid obtained in Example 9 was suspended in a 8 mL of 2-propanol and 2 mL of 2-butanone, followed by stirring at 30° C. for 8 hours. The crystal was collected by filtration and then dried under reduced pressure at 30° C. for an hour. XRD and IR revealed that resulting crystal is a 2-propanolate crystal. The yield was 90%.

Example 18

Production of Crystal D by Transition of Crystal B of 4-(1-((4-methylbenzothiophen-3-yl)methyl)benzimidazol-2-ylthio)butanoic acid 10 g of a crystal B and 100 mg of a crystal D of 4-(1-((4-methylbenzothiophen-3-yl)methyl)benzimidazol-2-ylthio)butanoic acid were suspended in 120 mL of 2-butanone, followed by stirring in an oil bath at 75° C. for 24 hours. After cooling to 20° C. at a rate of about 10° C./hour while stirring in an oil bath, the crystal was collected by filtration and then dried under reduced pressure at 60° C. for 4 hours. XRD and IR revealed that the resulting crystal is a crystal D. The yield was 90%. The melting peak temperature measured by DSC was 184° C.

INDUSTRIAL APPLICABILITY

It can be expected that the use of a crystal of 4-(1-((4-methylbenzothiophen-3-yl)methyl)benzimidazol-2-ylthio)butanoic acid of the present invention is advantageous for control of the storage stability and production process.

The invention claimed is:

1. A crystal of 4-(1-((4-methylbenzothiophen-3-yl)methyl)benzimidazol-2-ylthio)butanoic acid (crystal A), wherein the crystal form A is characterized by at least one of:
   (1) a crystal form A, which yields a powder X-ray diffraction pattern having characteristic peaks at reflection angles 2θ of approximately 9.0°, 15.2°, 16.4°, 19.2°, 20.6°, 22.3° and 22.6°;
   (2) a crystal form A, which yields a powder X-ray diffraction pattern as shown virtually in FIG. 1
   (3) a crystal form A, which has peaks at wave numbers of approximately 1711, 1442, 1285, 1252, 1204, 771 and 750 $cm^{-1}$ in an infrared absorption spectrum in potassium bromide; and
   (4) a crystal form A, which yields an absorption pattern as shown in FIG. 10 in an infrared absorption spectrum in potassium bromide.

2. A crystal of 4-(1-((4-methylbenzothiophen-3-yl)methyl)benzimidazol-2-ylthio)butanoic acid (crystal B), wherein the crystal form B is characterized by at least one of:
   (1) a crystal form B, which yields a powder X-ray diffraction pattern having characteristic peaks at reflection angles 2θ of approximately 14.1°, 17.7°, 18.6°, 22.3°, 23.5°, 24.3° and 26.2°;
   (2) a crystal form B, which yields a powder X-ray diffraction pattern as shown virtually in FIG. 2
   (3) a crystal form B, which has peaks at wave numbers of approximately 1716, 1701, 1290, 1252, 1207, 1151, 768 and 743 $cm^{-1}$ in an infrared absorption spectrum in potassium bromide; and
   (4) a crystal form B, which yields an absorption pattern as shown in FIG. 11 in an infrared absorption spectrum in potassium bromide.

3. A crystal of 4-(1-((4-methylbenzothiophen-3-yl)methyl)benzimidazol-2-ylthio)butanoic acid (crystal D); wherein the crystal form D is characterized by at least one of:
   (1) a crystal form D, which yields a powder X-ray diffraction pattern having characteristic peaks at reflection angles 2θ of approximately 11.4°, 13.8°, 16.7°, 22.4°, 23.9° and 25.5°;
   (2) a crystal form D, which yields a powder X-ray diffraction pattern as shown virtually in FIG. 3
   (3) a crystal form D, which has peaks at wave numbers of approximately 1703, 1441, 1383, 1321, 1245, 1196, 766 and 746 $cm^{-1}$ in an infrared absorption spectrum in potassium bromide; and
   (4) a crystal form D, which yields an absorption pattern as shown in FIG. 12 in an infrared absorption spectrum in potassium bromide.

4. A crystal of 4-(1-((4-methylbenzothiophen-3-yl)methyl)benzimidazol-2-ylthio)butanoic acid (crystal E), wherein the crystal form E is characterized by at least one of:
   (1) a crystal form E, which yields a powder X-ray diffraction pattern having characteristic peaks at reflection angles 2θ of approximately 16.4°, 16.8°, 19.6°, 20.4°, 21.5°, 22.6°, 23.4° and 24.1°;
   (2) a crystal form E, which yields a powder X-ray diffraction pattern as shown virtually in FIG. 4
   (3) a crystal form E, which has peaks at wave numbers of approximately 1716, 1286, 1221, 1196, 1144, 761 and 742 $cm^{-1}$ in an infrared absorption spectrum in potassium bromide; and
   (4) a crystal form E, which yields an absorption pattern as shown in FIG. 13 in an infrared absorption spectrum in potassium bromide.

5. A crystal of 4-(1-((4-methylbenzothiophen-3-yl)methyl)benzimidazol-2-ylthio)butanoic acid hydrate (hydrate crystal), wherein the hydrate crystal is characterized by at least one of:
   (1) a hydrate crystal, which yields a powder X-ray diffraction pattern having characteristic peaks at reflection angles 2θ of approximately 10.3°, 15.2°, 15.8°, 21.0°, 23.1°, 24.2° and 25.1°;
   (2) a hydrate crystal, which yields a powder X-ray diffraction pattern as shown virtually in FIG. 5
   (3) a hydrate crystal, which has peaks at wave numbers of approximately 1705, 1310, 1288, 1248, 1194, 760 and 746 $cm^{-1}$ in an infrared absorption spectrum in potassium bromide; and
   (4) a hydrate crystal, which yields an absorption pattern as shown in FIG. 14 in an infrared absorption spectrum in potassium bromide.

6. A crystal of 4-(1-((4-methylbenzothiophen-3-yl)methyl)benzimidazol-2-ylthio)butanoic acid methanolate (methanolate crystal), wherein the methanolate crystal is characterized by at least one of:
   (1) a methanolate crystal, which yields a powder X-ray diffraction pattern having characteristic peaks at reflection angles 2θ of approximately 7.8°, 12.4°, 17.3°, 25.0° and 25.8°;
   (2) a methanolate crystal, which yields a powder X-ray diffraction pattern as shown virtually in FIG. 6
   (3) a methanolate crystal, which has peaks at wave numbers of approximately 1728, 1444, 1250, 1190, 1038, 764 and 748 $cm^{-1}$ in an infrared absorption spectrum in potassium bromide; and
   (4) a methanolate crystal, which yields an absorption pattern as shown in FIG. 15 in an infrared absorption spectrum in potassium bromide.

7. A crystal of 4-(1-((4-methylbenzothiophen-3-yl)methyl)benzimidazol-2-ylthio)butanoic acid ethanolate (ethanolate crystal), wherein the ethanolate crystal is characterized by at least one of:
   (1) an ethanolate crystal, which yields a powder X-ray diffraction pattern having characteristic peaks at reflection angles 2θ of approximately 7.8°, 12.1°, 17.2°, 20.4°, 20.6°, 22.9°, 24.4° and 25.5°;
   (2) an ethanolate crystal, which yields a powder X-ray diffraction pattern as shown virtually in FIG. 7
   (3) an ethanolate crystal, which has peaks at wave numbers of approximately 1724, 1444, 1250, 1194, 1047, 766 and 746 $cm^{-1}$ in an infrared absorption spectrum in potassium bromide; and
   (4) an ethanolate crystal, which yields an absorption pattern as shown in FIG. 16 in an infrared absorption spectrum in potassium bromide.

8. A crystal of 4-(1-((4-methylbenzothiophen-3-yl)methyl)benzimidazol-2-ylthio)butanoic acid 1-propanolate (1-propanolate crystal), wherein the 1-propanolate crystal is characterized by at least one of:

(1) a 1-propanolate crystal, which yields a powder X-ray diffraction pattern having characteristic peaks at reflection angles 2θ of approximately 7.7°, 12.1°, 17.1°, 20.5°, 22.4° and 25.0°;

(2) a 1-propanolate crystal, which yields a powder X-ray diffraction pattern as shown virtually in FIG. 8

(3) a 1-propanolate crystal, which has peaks at wave numbers of approximately 1722, 1444, 1252, 1195, 974, 764 and 744 cm$^{-1}$ in an infrared absorption spectrum in potassium bromide; and (4) a 1-propanolate crystal, which yields an absorption pattern as shown in FIG. 17 in an infrared absorption spectrum in potassium bromide.

9. A crystal of 4-(1-((4-methylbenzothiophen-3-yl)methyl)benzimidazol-2-ylthio)butanoic acid 2-propanolate (2-propanolate crystal), wherein the 2-propanolate crystal is characterized by at least one of:

(1) a 2-propanolate crystal, which yields a powder X-ray diffraction pattern having characteristic peaks at reflection angles 2θ of approximately 7.8°, 12.0°, 17.1°, 20.1°, 20.6°, 22.7°, 24.0° and 25.2°;

(2) a 2-propanolate crystal, which yields a powder X-ray diffraction pattern as shown virtually in FIG. 9

(3) a 2-propanolate crystal, which has peaks at wave numbers of approximately 1722, 1444, 1250, 1198, 953, 766 and 744 cm$^{-1}$ in an infrared absorption spectrum in potassium bromide; and (4) a 2-propanolate crystal, which yields an absorption pattern as shown in FIG. 18 in an infrared absorption spectrum in potassium bromide.

10. A process for producing a crystal B according to claim 2, which comprises performing cooling crystallization from a solution of 4-(1-((4-methylbenzothiophen-3-yl)methyl)benzimidazol-2-ylthio)butanoic acid, and acetic acid, tetrahydrofuran, methanol, 2-butanone, water, or a mixed solvent of two or more kinds selected from them.

11. A process for producing a crystal B according to claim 2, which comprises adding a small amount of the crystal B as a seed crystal in cooling crystallization from a solution of 4-(1-((4-methylbenzothiophen-3-yl)methyl)benzimidazol-2-ylthio)butanoic acid, and acetic acid, tetrahydrofuran, methanol, 2-butanone, water, or a mixed solvent of two or more kinds selected from them.

12. A process for producing a crystal D according to claim 3, which comprises adding a small amount of the crystal D as a seed crystal in cooling crystallization from a solution of 4-(1-((4-methylbenzothiophen-3-yl)methyl)benzimidazol-2-ylthio)butanoic acid, and acetic acid, tetrahydrofuran, methanol, 2-butanone, water, or a mixed solvent of two or more kinds selected from them.

13. A process for producing a crystal D according to claim 3, which comprises performing crystallization by adding water as a poor solvent, to an acetic acid solution of 4-(1-((4-methylbenzothiophen-3-yl)methyl)benzimidazol-2-ylthio)butanoic acid.

14. A process for producing a crystal D according to claim 3, which comprises performing crystallization by adding a nonpolar hydrocarbon as a poor solvent, to an acetic acid solution of 4-(1-((4-methylbenzothiophen-3-yl)methyl)benzimidazol-2-ylthio)butanoic acid.

15. The process for producing a crystal D according to claim 14, wherein the nonpolar hydrocarbon is pentane, hexane, cyclohexane, heptane, or a mixed solvent of two or more kinds selected from them.

16. A process for producing a crystal B according to claim 2, which comprises performing neutralization crystallization by adding acid to a solution of an alkali metal salt of 4-(1-((4-methylbenzothiophen-3-yl)methyl)benzimidazol-2-ylthio)butanoic acid and water, and tetrahydrofuran, methanol, 2-butanone, or a mixed solvent of two or more kinds selected from them while maintaining at about 50° C. or higher.

17. A process for producing a hydrate crystal according to claim 5, which comprises performing neutralization crystallization by adding acid to a solution of an alkali metal salt of 4-(1-((4-methylbenzothiophen-3-yl)methyl)benzimidazol-2-ylthio)butanoic acid and water, and tetrahydrofuran, methanol, 2-butanone, or a mixed solvent of two or more kinds selected from them while maintaining at about 40° C. or lower.

18. A process for producing a crystal E according to claim 4, which comprises drying a hydrate crystal of 4-(1-((4-methylbenzothiophen-3-yl)methyl)benzimidazol-2-ylthio)butanoic acid.

19. A process for producing a methanolate crystal according to claim 6, which comprises performing cooling crystallization from a solution of 4-(1-((4-methylbenzothiophen-3-yl)methyl)benzimidazol-2-ylthio)butanoic acid, and a solvent containing methanol as a main solvent.

20. A process for producing a methanolate crystal according to claim 6, which comprises contacting methanol with a crystal E or a hydrate crystal of 4-( 1-((4-methylbenzothiophen-3-yl)methyl)benzimidazol-2-ylthio)butanoic acid, or a mixture thereof.

21. A process for producing an ethanolate crystal according to claim 7, which comprises performing cooling crystallization from a solution of 4-(1-((4-methylbenzothiophen-3-yl)methyl)benzimidazol-2-ylthio)butanoic acid, and a solvent containing ethanol as a main solvent.

22. A process for producing an ethanolate crystal according to claim 7, which comprises contacting ethanol with a crystal E or a hydrate crystal of 4-(1-((4-methylbenzothiophen-3-yl)methyl)benzimidazol-2-ylthio)butanoic acid, or a mixture thereof.

23. A process for producing a 1-propanolate crystal according to claim 8, which comprises performing cooling crystallization from a solution of 4-(1-((4-methylbenzothiophen-3-yl)methyl)benzimidazol-2-ylthio)butanoic acid, and a solvent containing 1-propanol as a main solvent.

24. A process for producing a 1-propanolate crystal according to claim 8, which comprises contacting 1-propanol with a crystal E or a hydrate crystal of 4-(1((4methylbenzothiophen-3-yl)methyl)benzimidazol-2-ylthio)butanoic acid, or a mixture thereof.

25. A process for producing a 2-propanolate crystal according to claim 9, which comprises performing cooling crystallization from a solution of 4-(1-((4-methylbenzothiophen-3-yl)methyl)benzimidazol-2-ylthio)butanoic acid, and a solvent containing 2-propanol as a main solvent.

26. A process for producing a 2-propanolate crystal according to claim 9, which comprises contacting 2-propanol with a crystal E or a hydrate crystal of 4-(1-((4-methylbenzothiophen-3-yl)methyl)benzimidazol-2-ylthio)butanoic acid, or a mixture thereof.

27. A process for producing a crystal D according to claim 3, which comprises suspending a crystal of 4-(1-((4-methylbenzothiophen-3-yl)methyl)benzimidazol-2-ylthio)butanoic acid or a solvate thereof, or a mixed crystal of two or more kinds selected from them in acetic acid, methyl acetate, ethyl acetate, propyl acetate, isopropyl acetate, butyl acetate, 4-methyl-2-pentanone, 2-butanone, acetone, tetrahydrofuran, acetonitrile, hexane, cyclohexane, heptane, toluene, xylene, methanol, ethanol, 1-propanol, 2-propanol, water, or a mixed solvent of two or more kinds selected from them.

\* \* \* \* \*